(12) United States Patent
McHugo et al.

(10) Patent No.: US 10,765,545 B2
(45) Date of Patent: *Sep. 8, 2020

(54) SUTURE ESOPHAGEAL STENT INTRODUCER

(71) Applicant: Cook Medical Technologies LLC, Bloomington, IN (US)

(72) Inventors: Vincent McHugo, Tipperary (IE); Triona Campbell, Killaloe (IE); Gerard Treacy, Limerick (IE); Melissa Anenden, Limerick (IE); Criostoir O. Bhealtun, Trim (IE)

(73) Assignee: Cook Medical Technologies LLC, Bloomington, IN (US)

( * ) Notice: Subject to any disclaimer, the term of this patent is extended or adjusted under 35 U.S.C. 154(b) by 211 days.

This patent is subject to a terminal disclaimer.

(21) Appl. No.: 15/797,892

(22) Filed: Oct. 30, 2017

(65) Prior Publication Data

US 2018/0116840 A1    May 3, 2018

Related U.S. Application Data

(60) Provisional application No. 62/415,302, filed on Oct. 31, 2016.

(51) Int. Cl.
*A61F 2/962* (2013.01)
*A61F 2/90* (2013.01)
(Continued)

(52) U.S. Cl.
CPC ............... *A61F 2/962* (2013.01); *A61F 2/07* (2013.01); *A61F 2/90* (2013.01); *A61F 2/954* (2013.01);
(Continued)

(58) Field of Classification Search
CPC ...... A61F 2002/9511; A61F 2002/9665; A61F 2/90; A61F 2002/9517; A61F 2/95; A61F 2/966; A61F 2002/9505; A61F 2002/9522
See application file for complete search history.

(56) References Cited

U.S. PATENT DOCUMENTS

| 5,183,504 A | 2/1993 | Kuwajima et al. |
| 5,693,083 A | 12/1997 | Baker et al. |

(Continued)

FOREIGN PATENT DOCUMENTS

| WO | 2008066923 A1 | 6/2008 |
| WO | 2015075708 A1 | 5/2015 |

OTHER PUBLICATIONS

U.S. Appl. No. 15/797,877, filed Oct. 30, 2017 Office Action dated Sep. 13, 2019.
(Continued)

*Primary Examiner* — Katherine M Shi
(74) *Attorney, Agent, or Firm* — Brinks Gilson & Lione

(57) ABSTRACT

A stent delivery system includes an elongate shaft including a proximal portion, a distal portion, at least one lumen extending at least partially therethrough, and a stent receiving portion on the distal portion of the elongate shaft. A stent is positioned on the stent receiving portion of the elongate shaft, the stent having a first configuration and a second configuration. A proximal constraining arrangement is engaged with a proximal end of the stent. A distal constraining arrangement is engaged with a distal end of the stent. The stent delivery system includes a handle assembly comprising a first shuttle operably connected to the proximal constraining arrangement and a second shuttle operably connected to the distal constraining arrangement. A brake
(Continued)

assembly positioned is within the handle assembly, the proximal constraining arrangement being coupled to a portion of the brake assembly.

14 Claims, 20 Drawing Sheets

(51) Int. Cl.
*A61F 2/07* (2013.01)
*A61F 2/95* (2013.01)
*A61F 2/954* (2013.01)

(52) U.S. Cl.
CPC ..... *A61F 2/9517* (2020.05); *A61F 2002/9511* (2013.01); *A61F 2002/9534* (2013.01)

(56) References Cited

U.S. PATENT DOCUMENTS

| | | |
|---|---|---|
| 5,843,162 A | 12/1998 | Inoue |
| 6,168,616 B1 | 1/2001 | Brown, III |
| 6,761,733 B2 | 7/2004 | Chobotov et al. |
| 7,993,383 B2 | 8/2011 | Hartley et al. |
| 8,016,869 B2 | 9/2011 | Nikolchev |
| 8,328,861 B2 | 12/2012 | Martin et al. |
| 9,168,136 B2 | 10/2015 | Yang et al. |
| 9,278,017 B2 | 3/2016 | Rasmussen et al. |
| 9,308,108 B2 | 4/2016 | McHugo |
| 9,603,696 B2 | 3/2017 | Hartley et al. |
| 9,889,028 B2 | 2/2018 | Rasmussen et al. |
| 2004/0073289 A1 | 4/2004 | Hartley |
| 2005/0107862 A1 | 5/2005 | Ohlenschlaeger |
| 2006/0142836 A1 | 6/2006 | Hartley et al. |
| 2006/0155366 A1 | 7/2006 | LaDuca |
| 2007/0167955 A1 | 7/2007 | Arnault de La Menardiere |
| 2008/0140178 A1 | 6/2008 | Rasmussen et al. |
| 2009/0099640 A1 | 4/2009 | Weng |
| 2009/0182405 A1 | 7/2009 | Arnault De La Menardiere |
| 2012/0239130 A1 | 9/2012 | Hartley et al. |
| 2012/0323302 A1 | 12/2012 | Brinser |
| 2013/0006346 A1 | 1/2013 | Costello |
| 2013/0090714 A1 | 4/2013 | McHugo |
| 2013/0289703 A1 | 10/2013 | Kinkade et al. |
| 2013/0289713 A1 | 10/2013 | Pearson et al. |
| 2014/0148895 A1 | 5/2014 | King |
| 2015/0335426 A1 | 11/2015 | Lim et al. |
| 2016/0184118 A1 | 6/2016 | Faber et al. |
| 2016/0270935 A1 | 9/2016 | Rasmussen et al. |
| 2018/0014954 A1 | 1/2018 | Bradway |
| 2018/0071124 A1 | 3/2018 | Davis et al. |
| 2018/0116839 A1 | 5/2018 | McHugo et al. |
| 2018/0116841 A1 | 5/2018 | McHugo et al. |
| 2018/0116845 A1 | 5/2018 | McHugo et al. |
| 2018/0116846 A1 | 5/2018 | McHugo et al. |
| 2018/0116847 A1 | 5/2018 | McHugo et al. |
| 2018/0116848 A1 | 5/2018 | McHugo et al. |
| 2018/0153721 A1 | 6/2018 | McHugo et al. |
| 2018/0193026 A1 | 7/2018 | Yang et al. |
| 2018/0311030 A1 | 11/2018 | Bradway |

OTHER PUBLICATIONS

U.S. Appl. No. 15/797,854, filed Oct. 30, 2017 Office Action dated Sep. 12, 2019.
U.S. Appl. No. 15/797,916, filed Oct. 30, 2017 Office Action dated Nov. 7, 2019.
U.S. Appl. No. 15/797,916, filed Oct. 30, 2017, Ex parte Quayle Action issued Jun. 12, 2019.
U.S. Appl. No. 15/797,877, filed Oct. 30, 2017, First Office Action dated Feb. 20, 2019.
U.S. Appl. No. 15/797,854, filed Oct. 30, 2017, First Office Action dated Feb. 14, 2019.
International Search Report dated Feb. 19, 2018 for PCT/US2017/059018 filed Oct. 30, 2017.
U.S. Appl. No. 15/797,864, filed Oct. 30, 2017 Office Action dated Dec. 9, 2019.
U.S. Appl. No. 15/797,838, filed Oct. 30, 2017 Office Action dated Jan. 7, 2020.
U.S. Appl. No. 15/797,916, filed Oct. 30, 2017 Notice of Allowance dated Feb. 24, 2020.
U.S. Appl. No. 15/797,877, filed Oct. 30, 2017 Office Action dated Mar. 10, 2020.
U.S. Appl. No. 15/797,928, filed Oct. 30, 2017 Office Action dated Apr. 1, 2020.

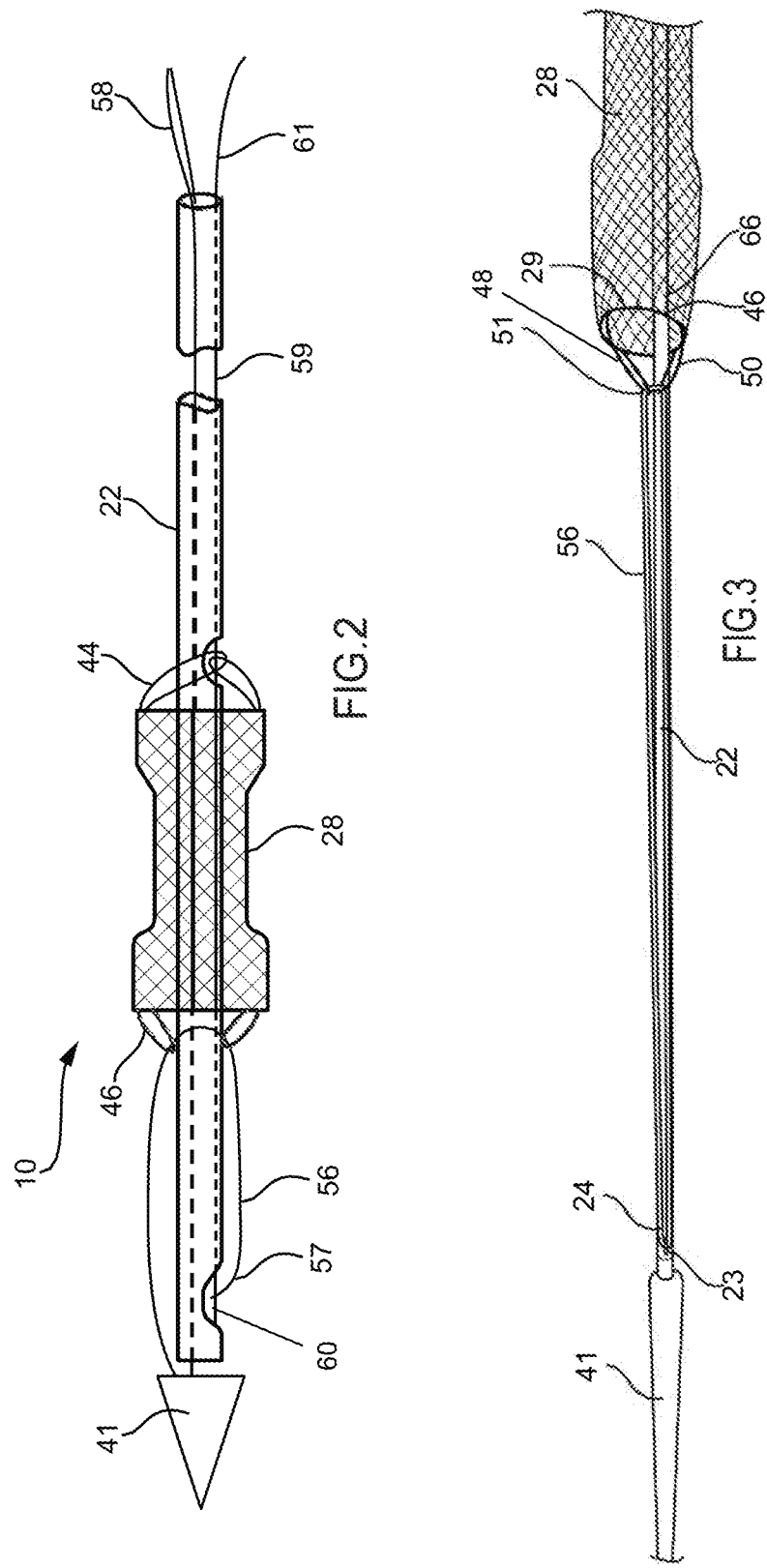

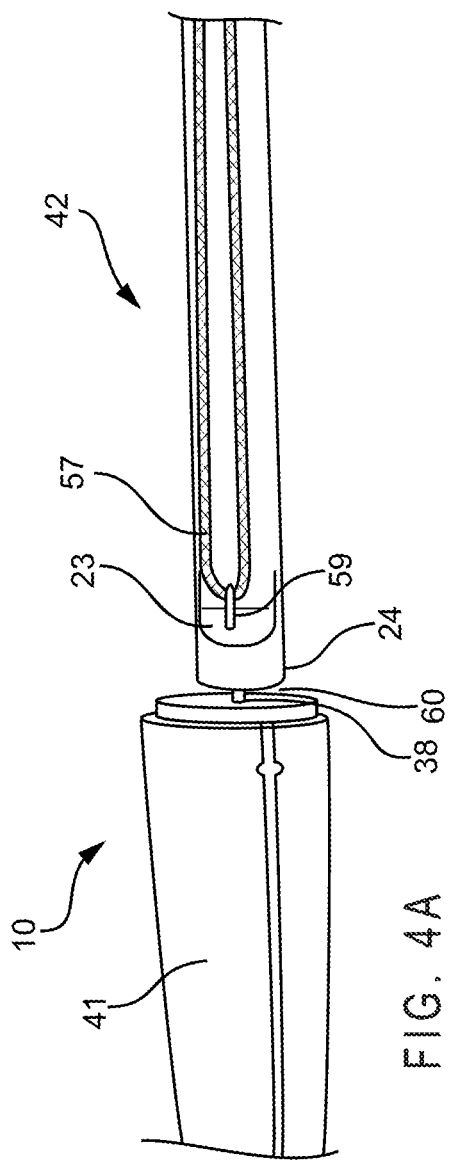
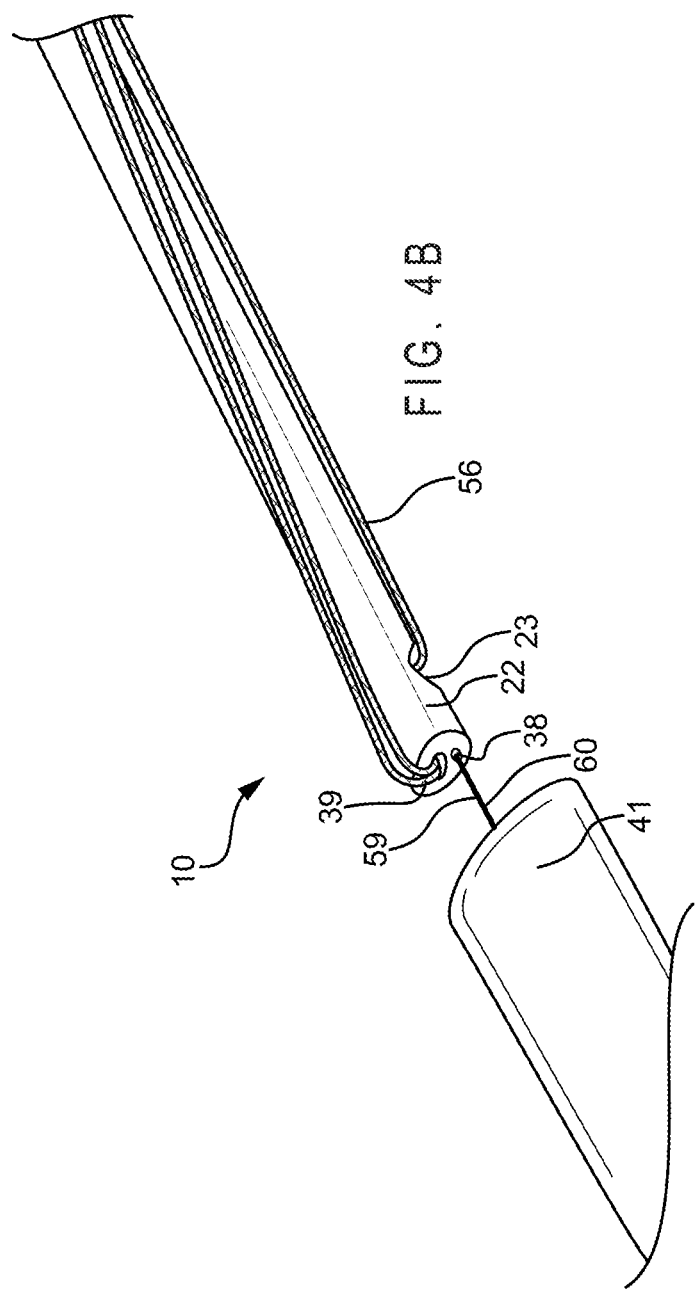

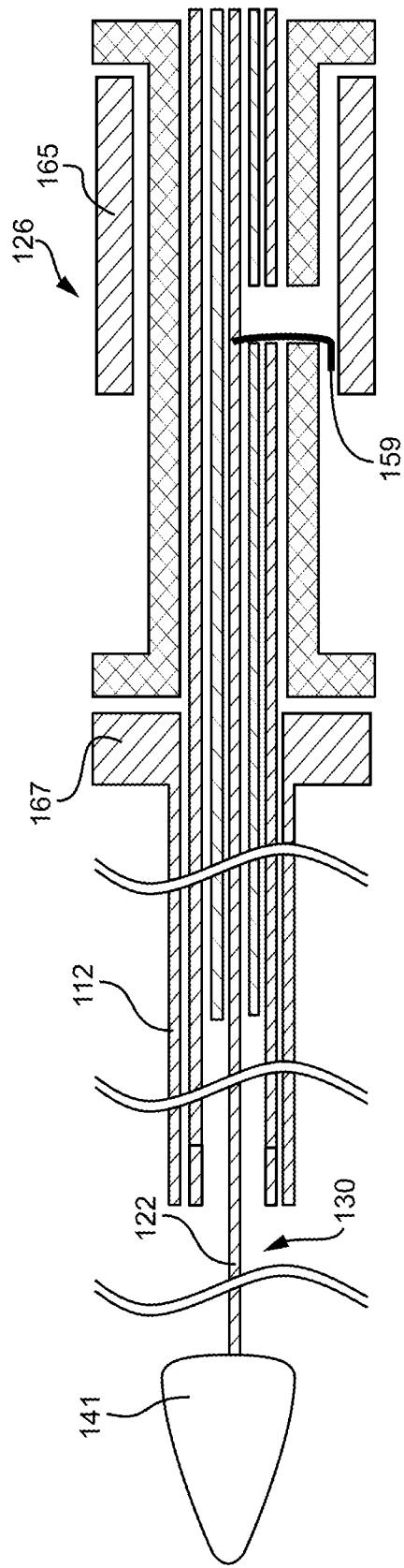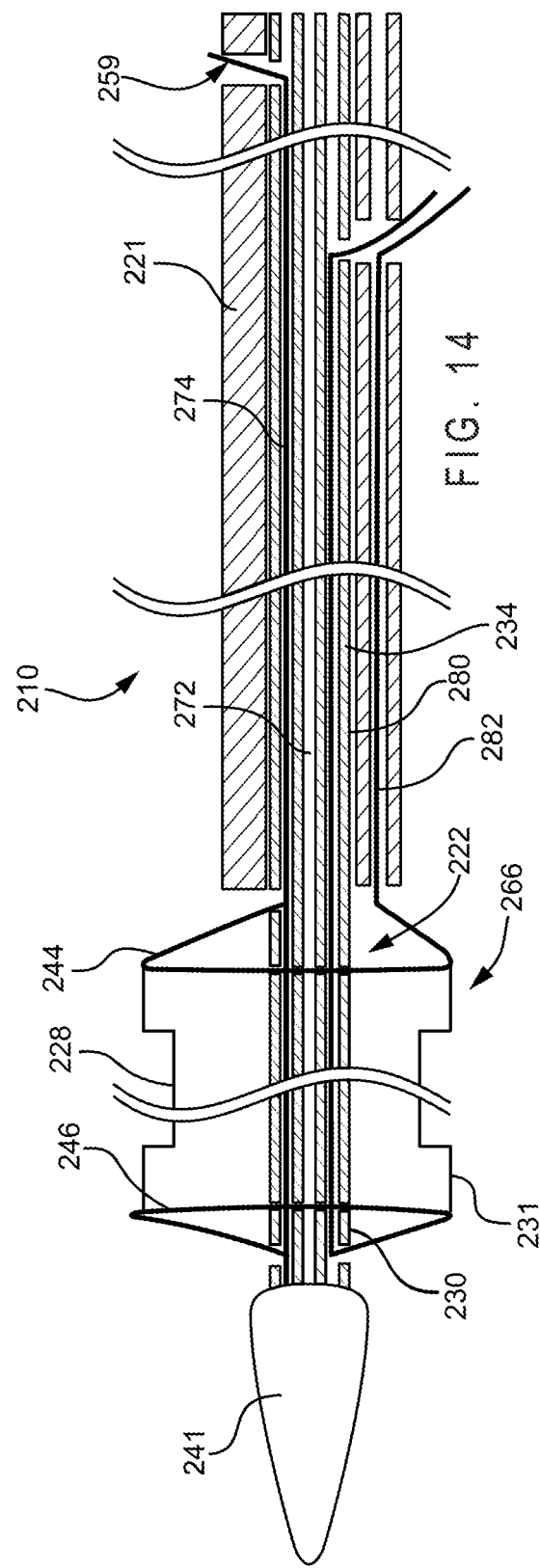

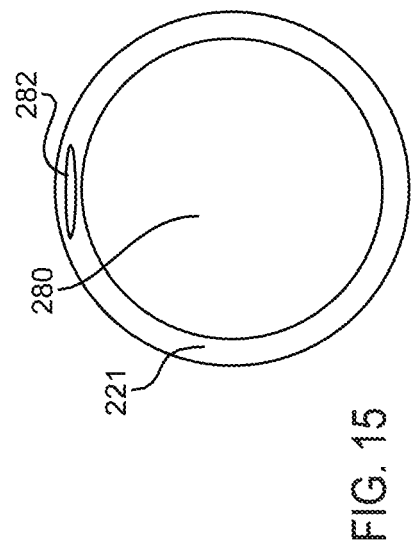
FIG. 15
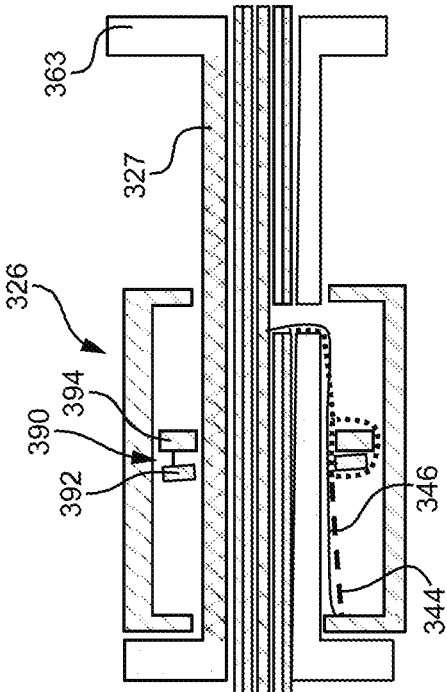
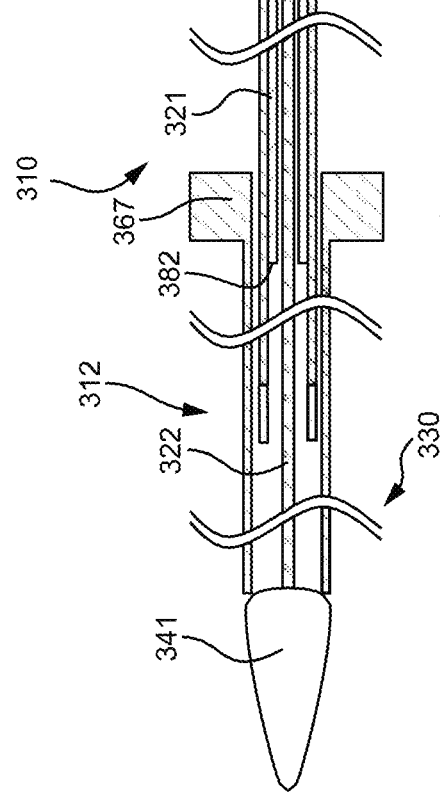
FIG. 16

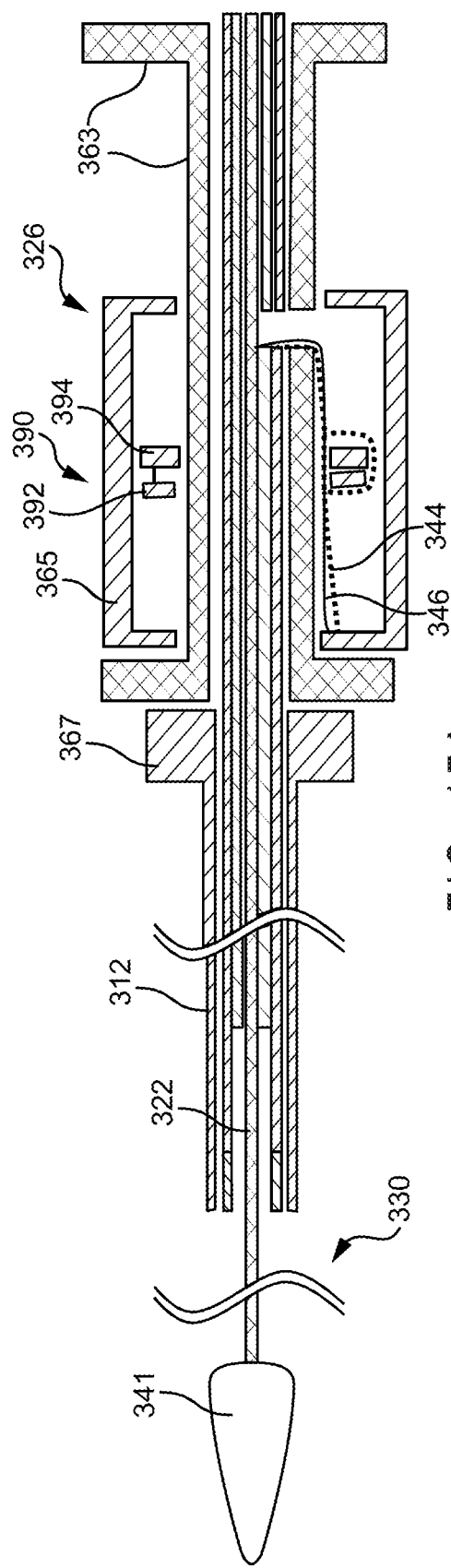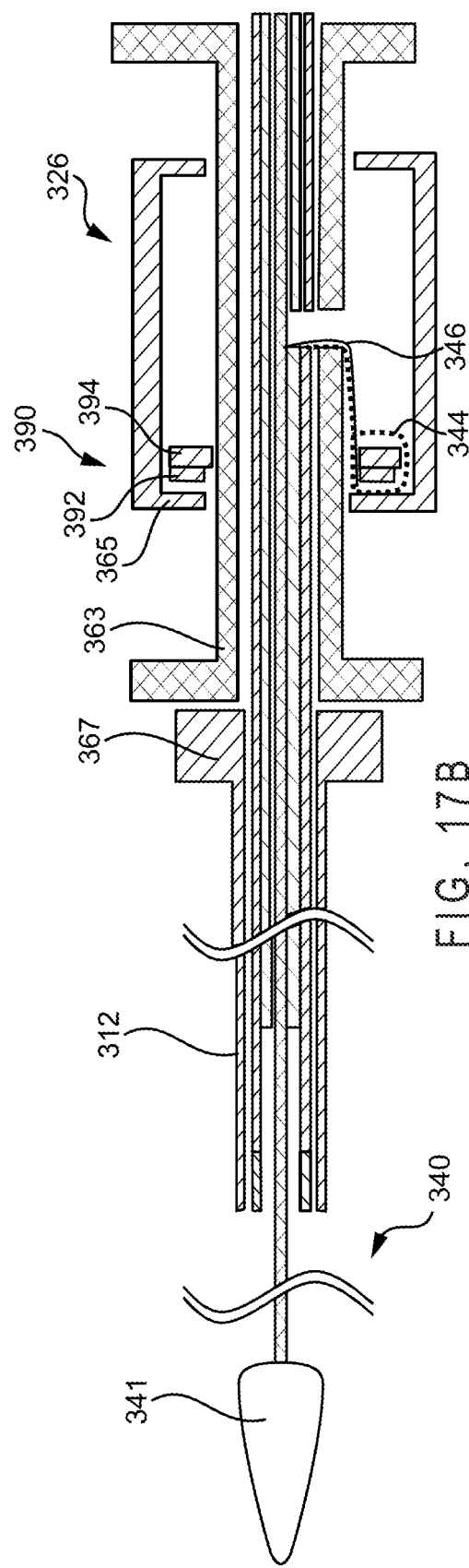
FIG. 17A
FIG. 17B

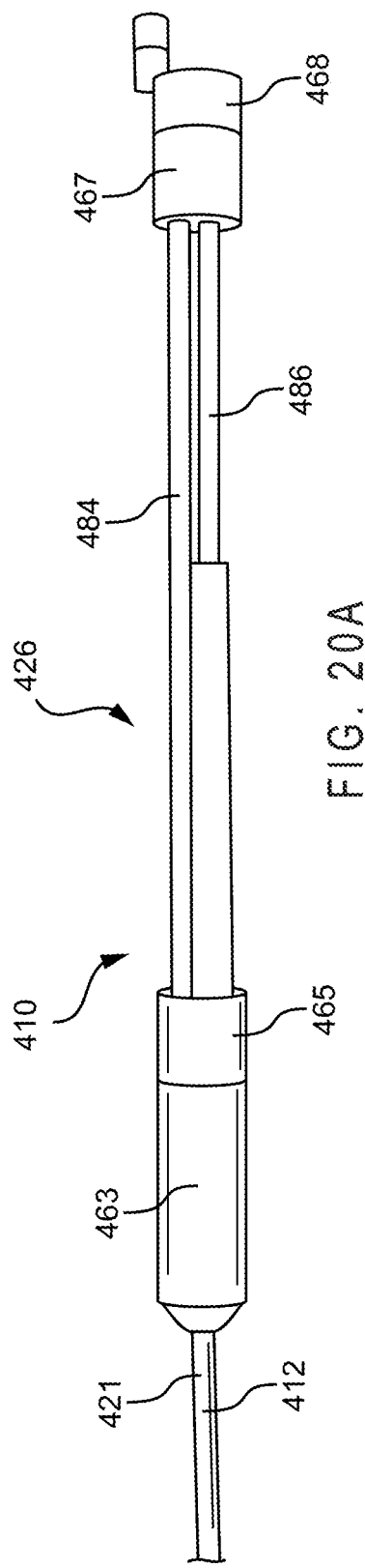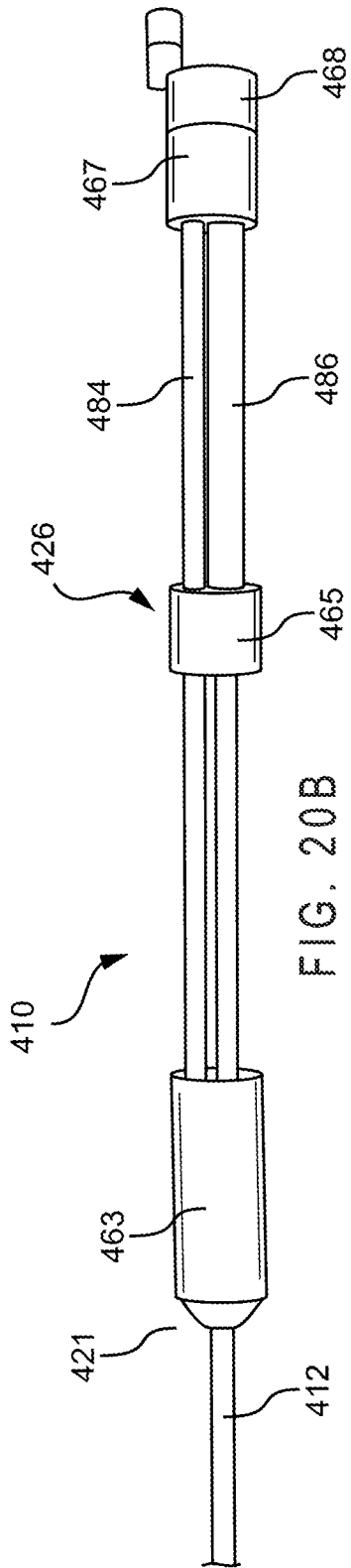
FIG. 20A
FIG. 20B

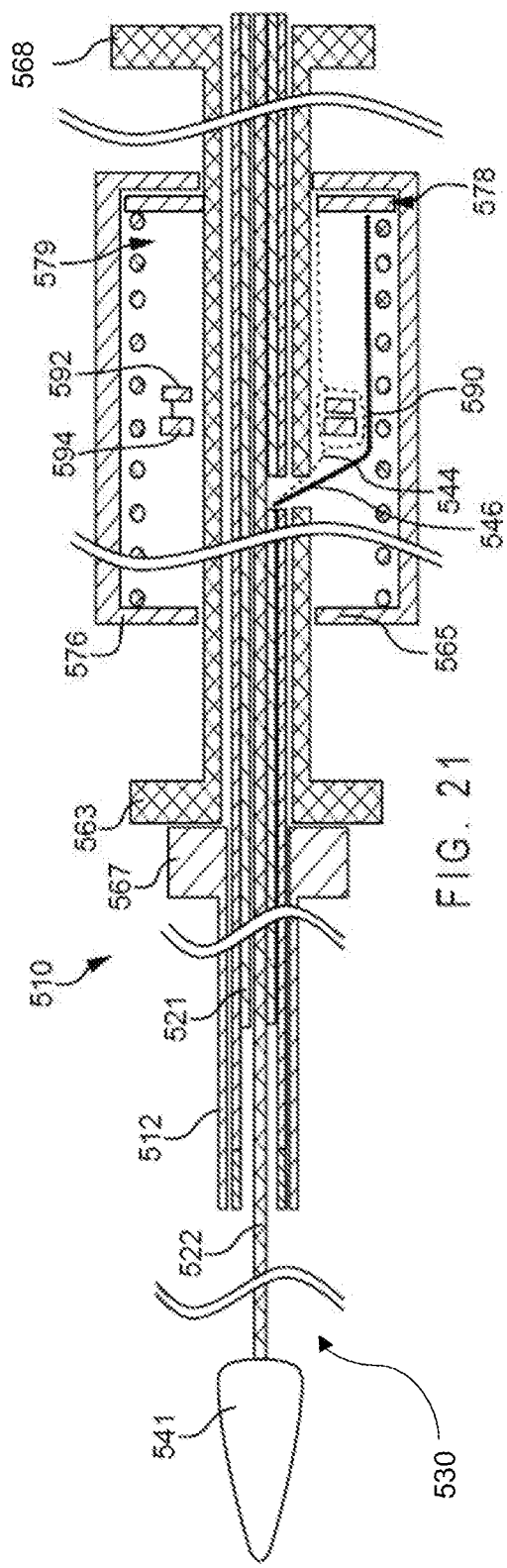
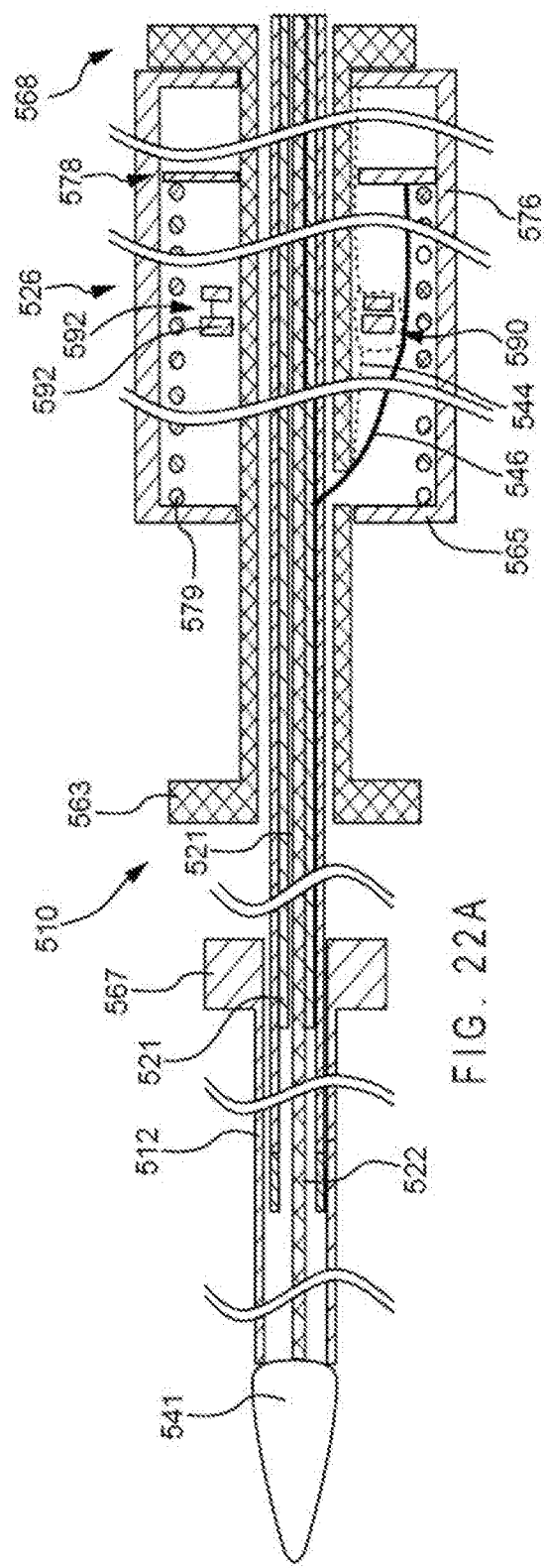

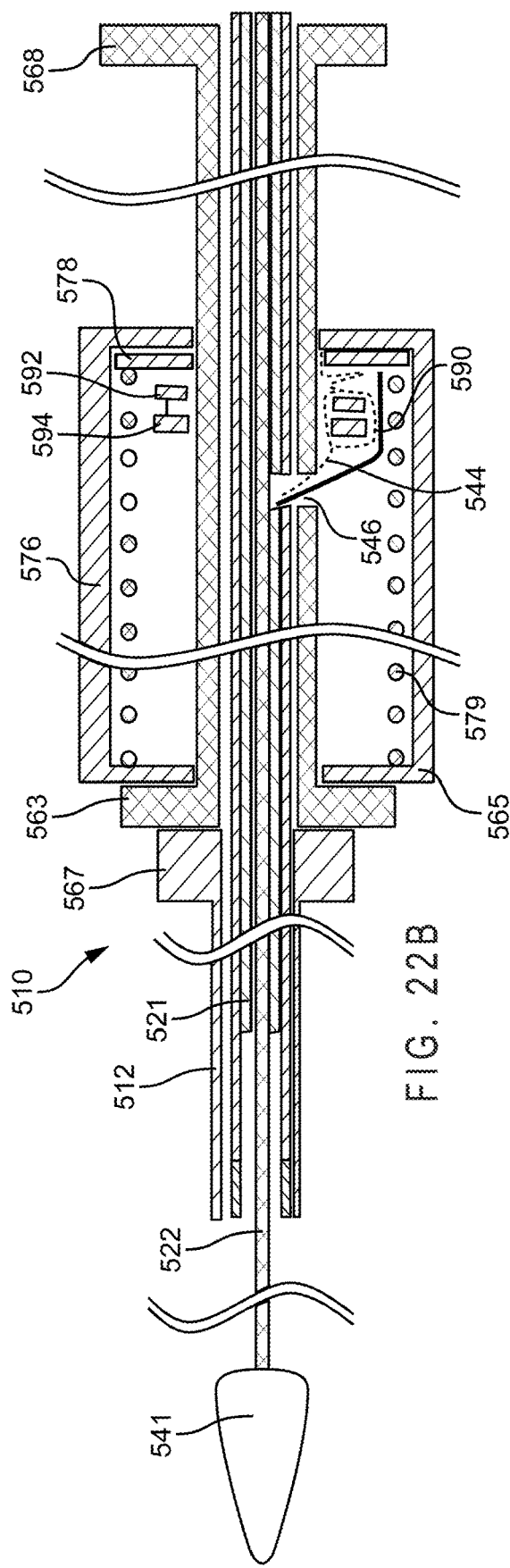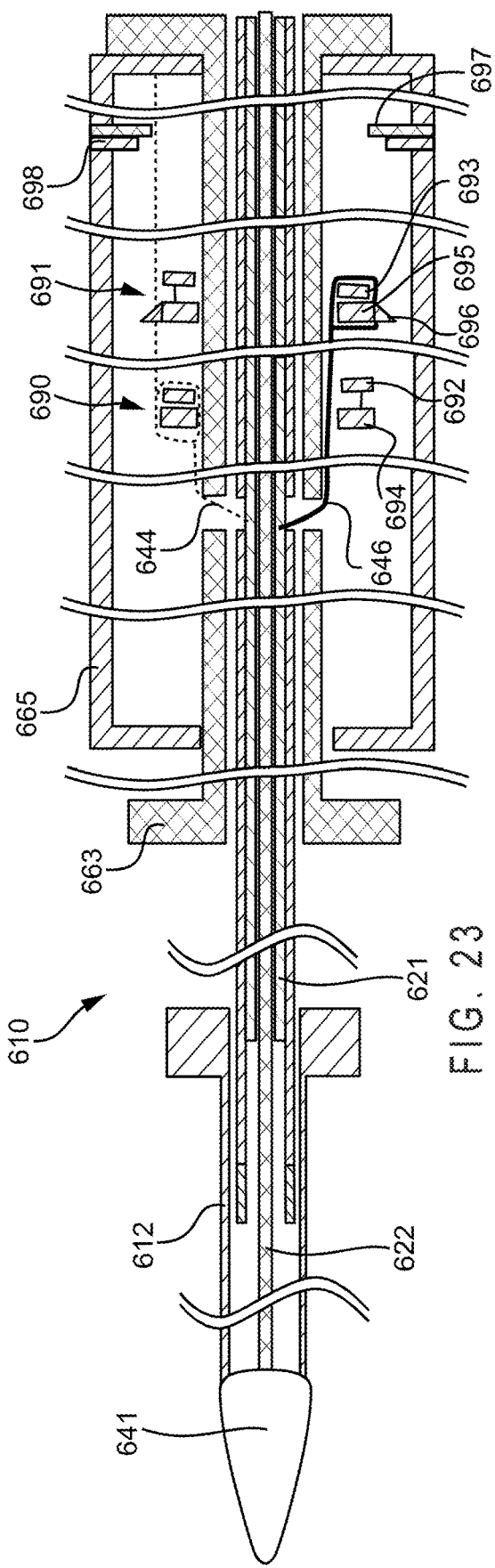

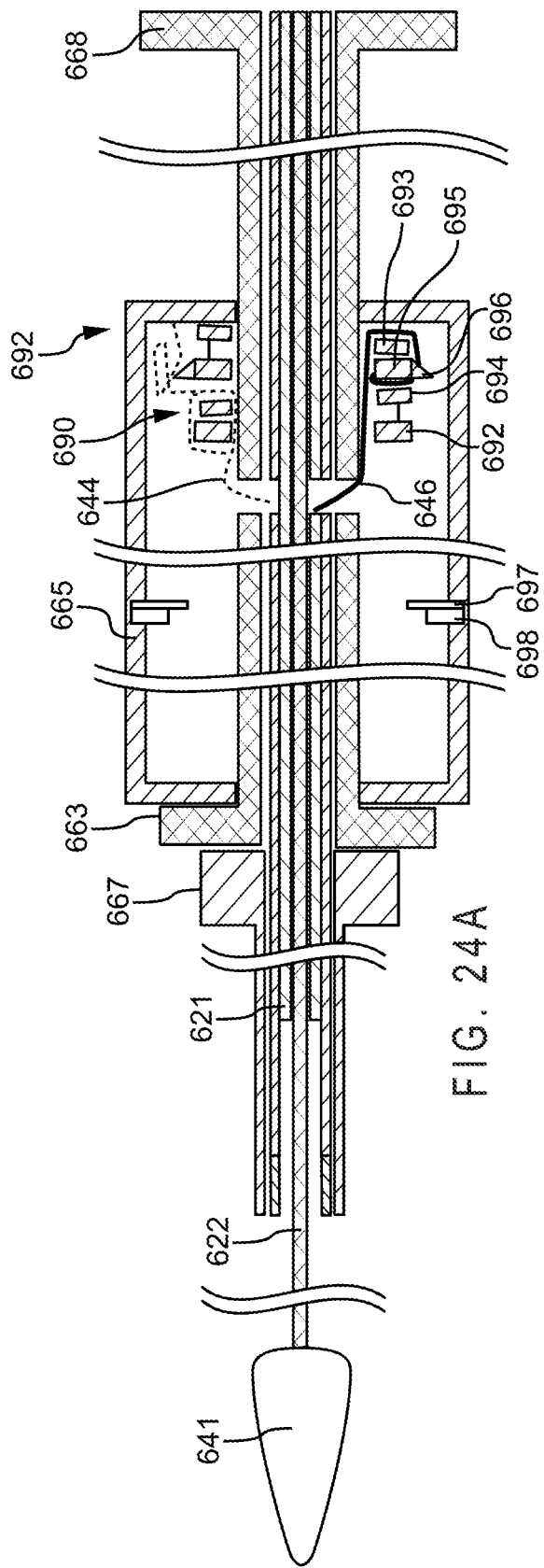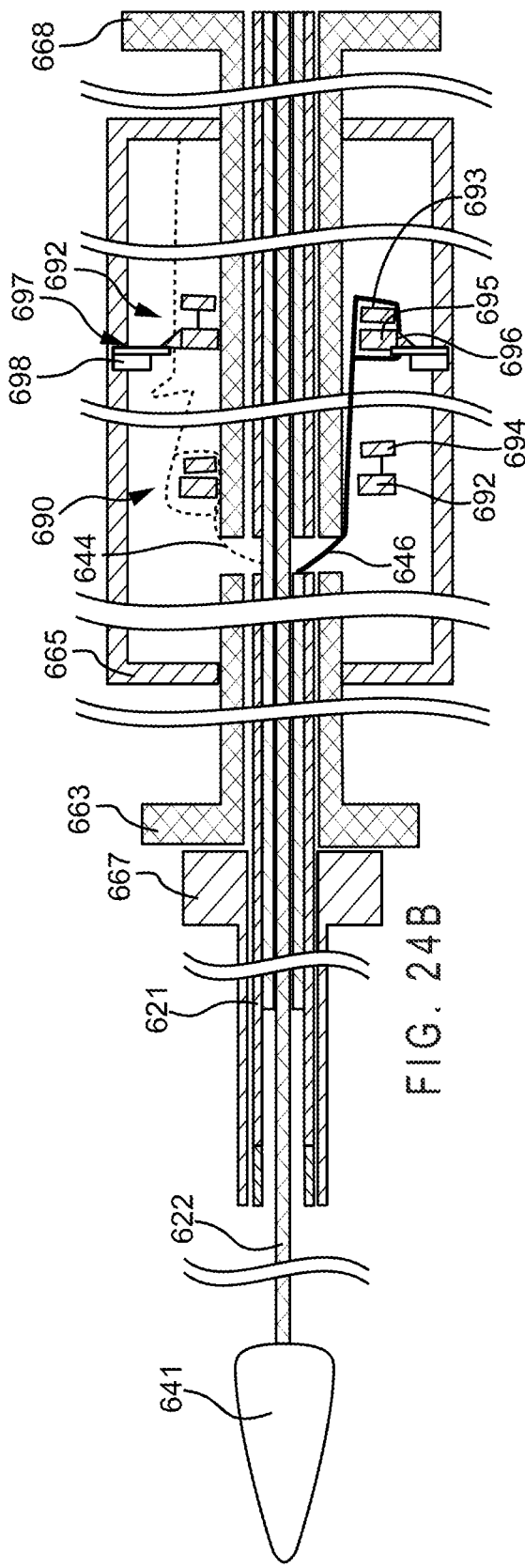

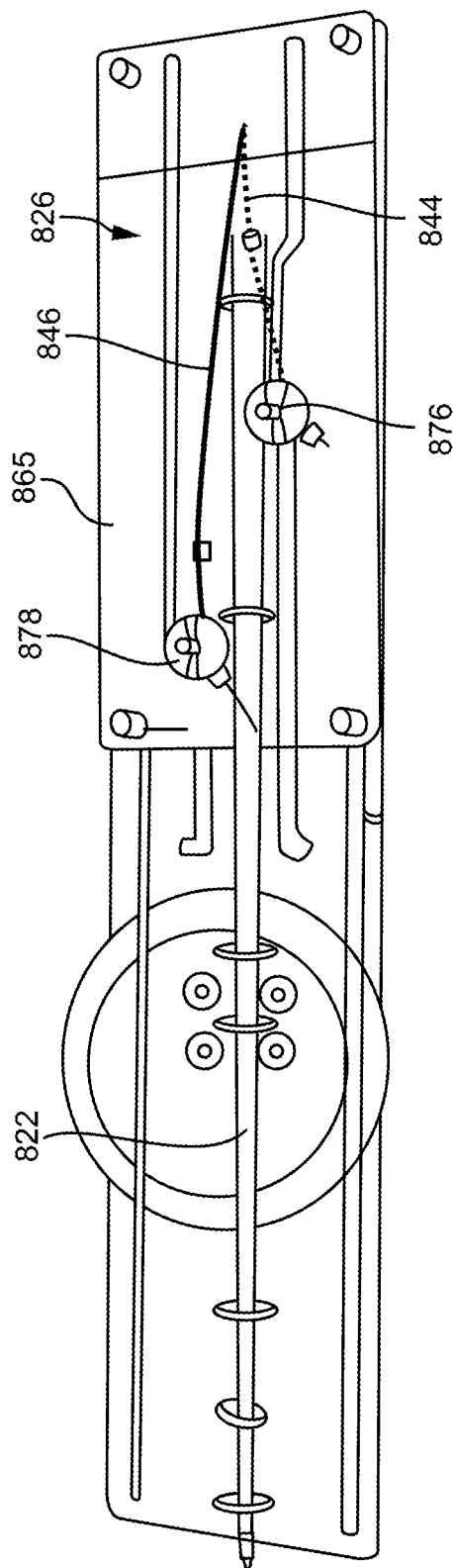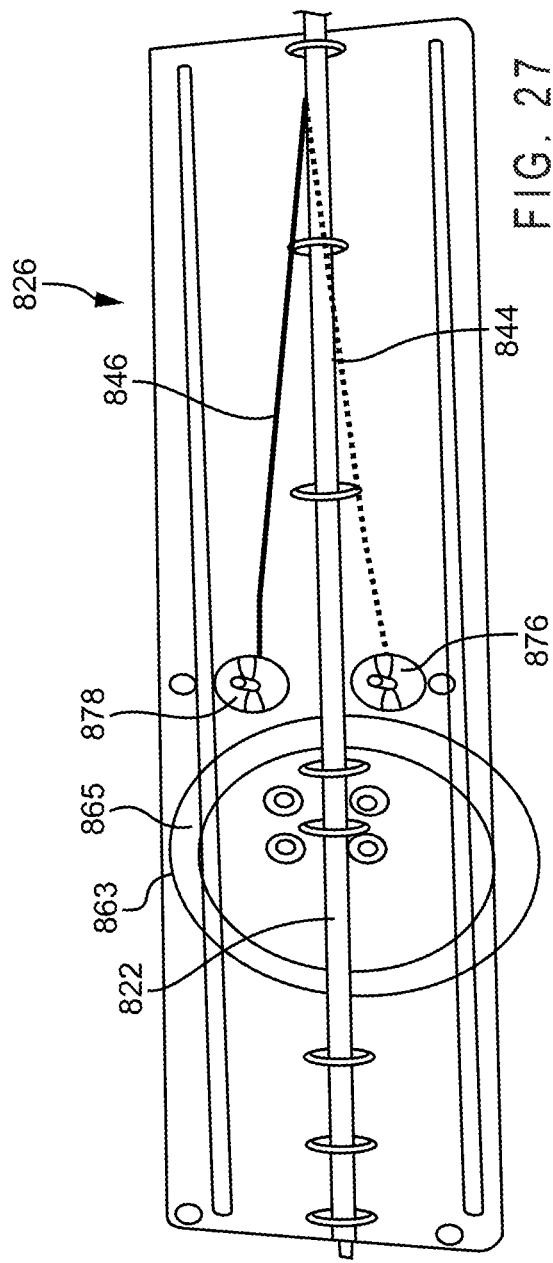

SUTURE ESOPHAGEAL STENT INTRODUCER

RELATED APPLICATION

This application claims the benefit of U.S. Provisional Patent Application Ser. No. 62/415,302 filed Oct. 31, 2016, which is incorporated by reference in its entirety.

BACKGROUND

1. Technical Field Text

This invention relates to a medical device, and in particular to a mechanically expandable device for delivering and deploying a stent or dilation and a method of delivering and deploying the stent into a body lumen.

2. Background Information

A self-expanding stent is typically introduced into the body using a delivery device that includes an outer sheath coaxially disposed and slidable over an inner catheter. The stent is disposed at the distal end of the device between the inner catheter and the outer sheath and held in a compressed position by the outer sheath. The inner catheter and the outer sheath move coaxially with respect to each other. The stent may be deployed by proximally pulling back the outer sheath relative to the inner catheter until the stent is exposed. The self-expanding stent expands from the stent distal end to the stent proximal end as the sheath is proximally withdrawn.

Several problems may occur with the sheathed delivery device described above. The sheath release delivery devices are difficult to reposition or remove and slow to operate. The stent may only be partially deployed prior to reconstrainment of the stent by the sheath in order to still reposition or remove the stent. Once the stent is fully deployed, i.e. readially expanded, the sheath cannot reconstrain the stent. For example, utilizing a conventional outer sheath/inner catheter delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen. Additionally, retraction of the outer sheath may not be achieved with controlled movement because the physician is manually retracting the outer sheath which may lead to uneven or inadvertent jerking back of the outer sheath that can lead to improper position of the stent.

Additionally, in a typical sheath release device where the outer sheath is proximally withdrawn, the first portion of the self-expanding stent to make contact with the body vessel is the most distal portion of the stent. This type of release may cause difficulty in accurately placing the proximal portion of the stent because the distal end of the stent is positioned first while the proximal portion of the stent is still covered by the outer sheath. Accurate placement of the proximal portion of the stent and/or the stent body may be important in certain applications, for example to prevent stent migration or to properly open a stricture along the entire length of the stricture. An additional drawback occurs with the sheathed stent delivery system where direct visualization of the stent is required. For example, in endoscopically placed stents, the sheath tends to prevent or obscure the location of the stent, making accurate placement of the stent more difficult.

Further potential drawbacks for the conventional sheathed stent delivery system involve the stent placement within the system prior to use within a patient. Loading and anchoring of a conventional sheathed stent delivery device is an involved process that may require preloading the stent into the device so that the stent remains compressed within the sheath during shipment and storage prior to use in the patient. Extended compression of the stent may lead to an alteration in the stent mechanical properties.

Conventional sheathed stent delivery devices also require a high force to overcome the friction between the stent and the sheath that may also be a problem for proper stent placement within the patient. The introducer must be mechanically stronger to overcome the frictional forces to avoid undesirable frictional consequences such as stretching of the introducer catchers and hysterics in the movement of the stent. The sheathed stent delivery device also requires more space within an endoscope compared to a sheathless device and also adds additional expense to the delivery system.

Accordingly, in view of the drawbacks of current technology, there is a desire for a mechanically expandable delivery system and dilation system that can increase the control, accuracy and ease of placement of a stent during deployment of the stent within a patient or dilation of a lumen within a patient. The delivery system would ideally reduce the risk of malfunction while providing for a smoother, more accurate and quicker deployment of the entire stent. The delivery system also would provide the ability to reconstrain, recapture, reposition and/or remove the stent after expansion of the stent.

BRIEF SUMMARY

Accordingly, it is an object of the present invention to provide a device and a method having features that resolve or improve on one or more of the above-described drawbacks.

The foregoing object is obtained in one aspect of the present invention by providing a stent delivery system. The stent delivery system includes an elongate shaft including a proximal portion, a distal portion, at least one lumen extending at least partially therethrough, and a stent receiving portion on the distal portion of the elongate shaft. A stent is positioned on the stent receiving portion of the elongate shaft, the stent having a first configuration and a second configuration. A proximal constraining arrangement is engaged with a proximal end of the stent, the proximal constraining arrangement comprising a first proximal constraining member having a proximal portion and a second proximal portion and a second proximal constraining member having a first proximal portion and a distal portion, the distal portion of the first proximal constraining member engaged with a first proximal portion of the stent and the distal portion of the second proximal constraining member engaged with a second proximal portion of the stent. A distal constraining arrangement is engaged with a distal end of the stent, the distal constraining arrangement comprising a first distal constraining member having a proximal portion and a second proximal portion and a second distal constraining member having a proximal portion and a distal portion, the distal portion of the first distal constraining member engaged with a first distal portion of the stent and the distal portion of the second proximal constraining member engaged with a second distal portion of the stent. A handle assembly comprising a first shuttle operably connected to the proximal constraining arrangement and a second shuttle operably connected to the distal constraining arrangement. A brake assembly is positioned within the handle assembly, the proximal constraining arrangement being coupled to the brake assembly. The proximal constraining arrangement and the distal constraining member applies an axial mechanical force to at least a portion of the stent in the first configuration.

In another aspect of the present invention, a method of implanting a stent in a patient's lumen is provided. The method includes inserting a distal portion of a stent delivery system into a lumen of a patient, the stent delivery system comprising: an elongate shaft including a proximal portion, a distal portion, at least one lumen extending at least partially therethrough, and a stent receiving portion on the distal portion of the elongate shaft. A stent is positioned on the stent receiving portion of the elongate shaft, the stent having a first configuration and a second configuration. A proximal constraining arrangement is engaged with a proximal end of the stent, the proximal constraining arrangement comprising a first proximal constraining member having a proximal portion and a second proximal portion and a second proximal constraining member having a proximal portion and a distal portion, the distal portion of the first proximal constraining member engaged with a first proximal portion of the stent and the distal portion of the second proximal constraining member engaged with a second distal portion of the stent. A distal constraining arrangement is engaged with a distal end of the stent, the distal constraining arrangement comprising a first distal constraining member having a proximal portion and a second proximal portion and a second distal constraining member having a proximal portion and a distal portion, the distal portion of the first distal constraining member engaged with a first distal portion of the stent and the distal portion of the second proximal constraining member engaged with a second proximal portion of the stent. A handle assembly comprising a first shuttle operably connected to the proximal constraining arrangement and a second shuttle operably connected to the distal constraining arrangement. A brake assembly is positioned within the handle assembly, the proximal constraining arrangement being coupled to a portion of the brake assembly. The method includes holding the stent in the first configuration with longitudinal tensile force applied to the stent by the proximal constraining member and the distal constraining member and tensioning the stent for delivery of the stent to an implant site. The method also includes positioning the stent at the implant site. The method further includes expanding the stent by manipulating the first shuttle and the second shuttle in a distal direction and releasing longitudinal force on the stent.

In another aspect of the present invention, a system is provided. The system includes an inner elongate shaft including a proximal portion, a distal portion, at least one lumen extending at least partially therethrough, and a stent receiving portion on the distal portion of the elongate shaft. The stent system includes an outer elongate having a proximal portion, a distal portion, at least one lumen extending at least partially therethrough, the inner elongate shaft extending coaxially at least partially within the lumen of the outer elongate shaft, the outer sheath moveably positionable relative to the inner elongate shaft. A stent is positioned on the stent receiving portion of the elongate shaft, the stent having a first configuration and a second configuration. A proximal constraining arrangement is engaged with a proximal end of the stent, the proximal constraining arrangement comprising a first proximal constraining member having a proximal portion and a second proximal portion and a second proximal constraining member having a proximal portion and a distal portion, the distal portion of the first proximal constraining member engaged with a first proximal portion of the stent and the distal portion of the second proximal constraining member engaged with a second proximal portion of the stent. A distal constraining arrangement is engaged with a distal end of the stent, the distal constraining arrangement comprising a first distal constraining member having a proximal portion and a second proximal portion and a second distal constraining member having a proximal portion and a distal portion, the distal portion of the first distal constraining member engaged with a first distal portion of the stent and the distal portion of the second proximal constraining member engaged with a second proximal portion of the stent. A release wire is disposed through the elongate shaft and releasably engaged with portion of the proximal constraining arrangement and the distal constraining arrangement member. A handle assembly comprising a first shuttle is operably connected to the proximal constraining arrangement and a second shuttle is operably connected to the distal constraining arrangement. A brake assembly is positioned within the handle assembly, the proximal constraining arrangement being coupled to a portion of the brake assembly. The proximal constraining arrangement and the distal constraining member applies an axial mechanical force to at least a portion of the stent in the first configuration.

BRIEF DESCRIPTION OF THE DRAWINGS

FIG. 2 illustrates a sectional view of the stent delivery system shown in FIG. 1.

FIG. 3. illustrates a distal end of the stent delivery system shown FIG. 1.

FIGS. 4A and 4B illustrate a first section of the distal end of the stent delivery system shown in FIGS. 1A and 1B.

FIG. 13A and FIG. 13B illustrates operation of the stent delivery system of FIG. 8.

FIG. 14 illustrates a sectional view of an alternate embodiment of a stent delivery system.

FIG. 15 illustrates a cross-section through an outer shaft of an embodiment of a stent delivery system.

FIG. 16 is a sectional view of the embodiment of the system of FIG. 14.

FIGS. 17A-17C illustrate operation of the embodiment of the system of FIG. 14.

FIGS. 20A and 20B illustrate operation of the embodiment of the handle assembly of FIG. 18.

FIG. 21 illustrates of schematic view of an alternative embodiment of a handle assembly of a stent delivery system.

FIGS. 22A and 22B illustrate operation of the embodiment of FIG. 21.

FIG. 23 illustrates of schematic view of an alternative embodiment of a handle assembly of a stent delivery system.

FIGS. 24A-24C illustrate operation of the embodiment of the system of FIG. 23.

FIG. 26 illustrates a schematic view of an alternative embodiment of a handle assembly of a stent delivery system.

FIG. 27 illustrates operation of this embodiment of the system of FIG. 26.

DETAILED DESCRIPTION OF THE DRAWINGS AND THE PRESENTLY PREFERRED EMBODIMENTS

Figure 1A:
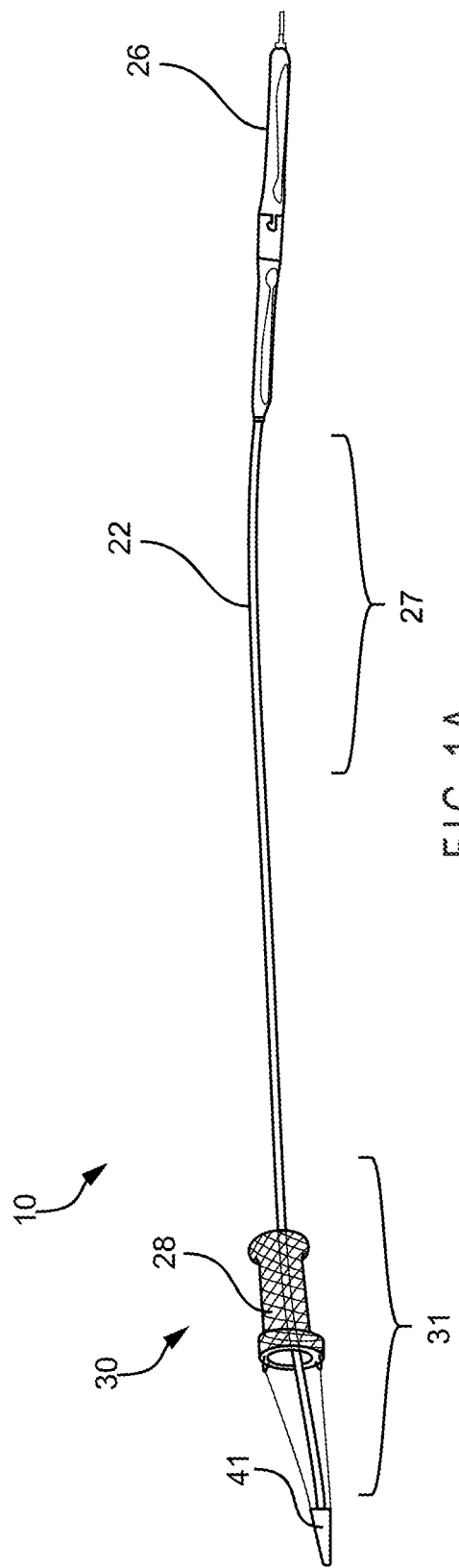
FIGS. 1A and 1B illustrate a stent delivery system 10 in accordance with embodiments of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

FIG. 1A illustrates a stent delivery system 10 in accordance with embodiments of the present invention. The stent delivery system 10 includes an inner shaft 22 and a handle 26 at a proximal portion 27 of the system 10. A stent 28 is positionable on a stent region 30 of the inner shaft 22 at a distal portion 31 of the delivery system 10. As shown, the stent 28 is in an expanded configuration 66. The stent delivery system 10 may optionally include an outer sheath slidably positionable over a portion the inner shaft 22 to cover the stent region 30 and the stent 28. The stent delivery system 10 may also include a guidewire extendable through a port of the inner shaft 22 through a distal tip 41 at the distal portion 31 of the delivery system 10. The stent 28 may be placed in a constrained position, as shown in FIG. 1B.

Figure 1B:
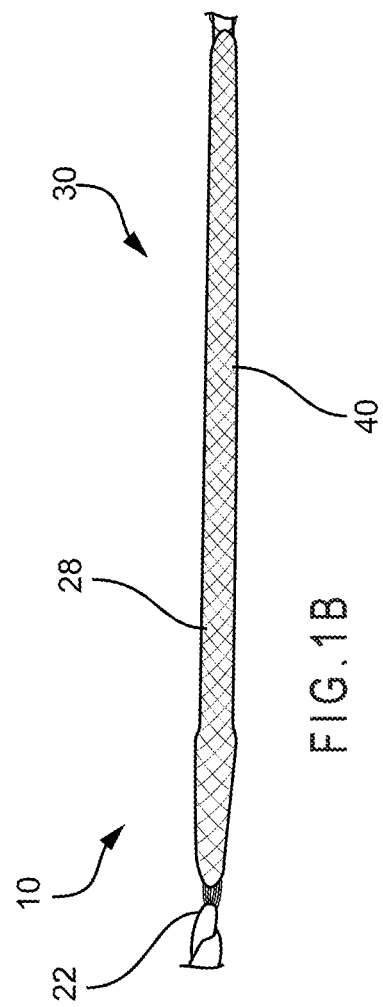

FIG. 2 illustrates a sectional view of the stent delivery system 10 shown in FIG. 1. As shown in FIG. 2, the stent 28 is in an expanded configuration 66 while still connected to the inner shaft 22. In some embodiments, the stent 28 may be a self-expanding stent. The stent 28 may be any kind of stent that has a tendency to radially collapse when a longitudinal force is applied to the ends of the stent. By way of non-limiting example, the stent 28 may be formed as a woven mesh formed from a metal or polymer or a laser cut pattern formed in a metal stent. The stent 28 may also be formed from a bioabsorbable material. One example of a woven stent is the EVOLUTION® stent (Wilson-Cook Medical, Inc.). The stent 28 is held in the constrained configuration 40 by a mechanism that may be provided with or without an outer sheath. In one embodiment that is described in detail below, that includes a proximal stent constraining member 44 and a distal stent constraining member 46 to longitudinally constrain the stent 28 and hold the stent 28 collapsed against the inner shaft 22. The proximal and distal stent constraining members 44, 46 are operably connected to the handle 26. In particular, the distal stent constraining member 46 is connected to the handle via a restraining member disposed through a port in the inner shaft 22. The restraining member 56 includes a proximal end 58 and a distal end 57. The restraining member 56 is releaseably connected to the distal constraining member 46. The proximal end 58 of the restraining member 56 is connected to the handle 26 of the stent delivery system 10. The restraining member 56 is configured to allow the user to move the distal end 33 of the stent 28 from a constrained configuration 40 (as shown in FIG. 1B) to an expanded configuration 66 without fully deploying the stent. The proximal stent constraining member 44 is connected to the handle 26 via release wire 59. The release wire 59 includes a distal end 60 and a proximal end 61. The proximal end 61 of the release wire 59 is connected to the handle 26 on a proximal end of the stent delivery system 10. As shown in the figures, the release wire releasably engages the proximal constraining member and releasably connects the proximal end of the stent to the inner shaft 22. The distal end 60 of the release wire 59 engages the distal end 57 of the restraining member 56 and releasably connect the distal end 60 of the release wire 59 to the inner shaft 22. As shown in FIG. 2, the stent 28 is held compressed against the inner shaft 22 by the proximal and distal stent constraining members 44, 46 in a first position 47 applying longitudinal force to the stent 28 in opposite directions. When present, an outer sheath may provide some compressive force to the stent in addition to the proximal and distal constraining members 44, 46.

FIG. 3. shows a view of the distal end of the system 10. As shown, the stent 28 is shown in an expanded configuration 66 in FIG. 3 where the stent 28 is expanded away from the inner shaft 22. The distal constraining members 46 is in a second position 49 and remain connected to the stent 28 but the longitudinal force on the stent 28 has been removed to allow the stent 28 to expand. The distal constraining member, in this embodiment, includes a pair of distal grasping loops 48, 50. The distal grasping loops 48, 50 may be interwoven through one or more peaks of the stent so that the distal grasping loops 48, 50 when pulled taut will collapse the peaks 29 of the stent 28 onto the inner shaft 22. The distal grasping loops 48, 50 may be positioned on opposing sides of the stent 28, as provided in this embodiment. In alternative embodiments, the grasping loops 48, 50 may be placed in different positions. The distal grasping loops 48, 50 of the distal constraining member 46 may be anchored at one or more points to better secure the stent 28 on the inner shaft 22. In other embodiments, the stent 28 may include a suture about the proximal end 31 and the distal end 33 of the stent 28. The grasping loops may be interwoven about the suture at the ends of the stent 28. In the embodiment shown in FIG. 3, the distal grasping loops 48, 50 are configured to remain attached to the stent 28 upon deployment within the lumen of a patient. In alternative embodiments, the distal grasping loops 48, 50 may be configured to be released from the stent upon deployment within the lumen of a patient.

As shown, the restraining member 56 extends within a first opening 23 disposed in the inner shaft 22 and exits from the port 38 at a distal end 24 of the inner shaft 22. In this embodiment, the restraining member 56 is a suture. One of skill in the art will understand other materials may be suitable for the restraining member 56. The restraining member 56 is configured to keep the distal end 33 of the stent 28 attached to the inner tube 22 prior to deployment within the lumen of a patient while allowing the stent 28 to be released from the constrained configuration 40 to the expanded configuration 66. As shown, the restraining member 56 exits from a port 38 at the distal end 24 of the inner shaft 22. In this embodiment, the restraining member 56 extends in a proximal direction and engages with a distal point 51 of the distal grasping loops 48, 50 of the distal constraining member 46. After exiting the distal grasping loops 48, 50 of the distal constraining member 46, the restraining member 56 extends in a distal direction and enters into a suture lumen 34 of inner tube 22 of the system 10 near the distal tip 41 of the system 10. Upon entering the lumen 34 of the inner tube 22 of the system 10, the restraining member 56 extends through the length of the inner tube 22 and engages with a handle 26. The handle 26 allows for control of the restraining member 56 in order to move the stent 28 from the constrained configuration 40 to the expanded configuration 66 so that the release of the tension on the stent 28 is uniform within the patient's lumen. The restraining member 56 moves the distal end 33 of the stent 28 so that the longitudinal tension exerted on the stent 28 is relaxed when the distal grasping loops of the distal constraining member 44 are further apart and the stent 28 expands uniformly due to the uniform release of the tension on the stent 28 by the distal constraining member 46.

The stent 28 may be repeatedly moved between the constrained configuration 40 and the expanded configuration 66 by manipulating the restraining member either in a proximal direction or a distal direction until the stent is properly positioned. With the stent repositioned in the constrained configuration 40, an outer sheath may be repositioned over the stent 28 as shown in FIG. 2 and the stent 28 may even be withdrawn from the patient, for example if an incorrect size of stent was originally selected. The stent configurations may be changed multiple times within the patient for repositioning or removal until the proximal and distal constraining members 44, 46 are released from connection with the stent 28 as described below.

FIGS. 4A and 4B illustrate the first section 42 of the distal end 24 of the system 10. As shown, the system 10 includes a distal tip 41, an inner shaft 22, a distal end portion 57 of the restraining member 56, and a distal end portion 60 of the release wire 59. The inner tube 22 includes an opening 23, where the distal end portion 57 of the restraining member 56 and the distal end portion 60 of the release wire 59 are disposed. The release wire 59 is releasably engaged within a lumen of the inner tube 22 and terminates proximal to the distal tip 41 of the system 10. In this embodiment, the distal end portion 57 of the restraining member 56 is anchored to the inner tube 22 by the release wire 59. The proximal portion the release wire (not shown) is engaged with a handle of the system. As will be discussed below, upon release of the release wire 59 by the user of the system 10, the proximal end of the restraining member is also released, allowing the distal end 33 of the stent 28 to be deployed within the lumen of the patient. In this embodiment, the restraining member 56 is a looped suture. In alternative embodiments, the restraining member 56 may have alternative configurations or materials, including a single suture. The release wire 59 may be frictionally engaged with a portion of the inner tube 22 of the system 10 to hold the release wire 59 in position until the stent 28 is in the proper position for release as discussed above. The release wire 59 may be proximally withdrawn to release the distal constraining member 46.

As shown in FIG. 4B, the system 10 includes an inner shaft 22, distal tip 41, and a distal end portion 57 of the restraining member 56. The inner shaft 22 further includes access to the suture lumen 34 of the inner tube 22 of the system 10. In this embodiment, the opening 23 in the inner shaft 22, where the distal end portion 57 of the restraining member 56 and the distal end portion 60 of the release wire 59 are disposed, is also visible. The release wire 59 is releasably engaged within a port 38 of the inner tube 22 and terminates proximal to the distal tip 41 of the system 10. The restraining member 56 enters into the inner tube 22 at a port 39 distal to the stent 28 and proximal of the distal tip 41. The second opening 39 is disposed distal to the first port 38 on the distal end of the system. As discussed above, the restraining member 56 enters into this second port 39 and extends to a handle, which allows for a user to manipulate the position of the distal end 33 of the stent 28.

Figure 5:
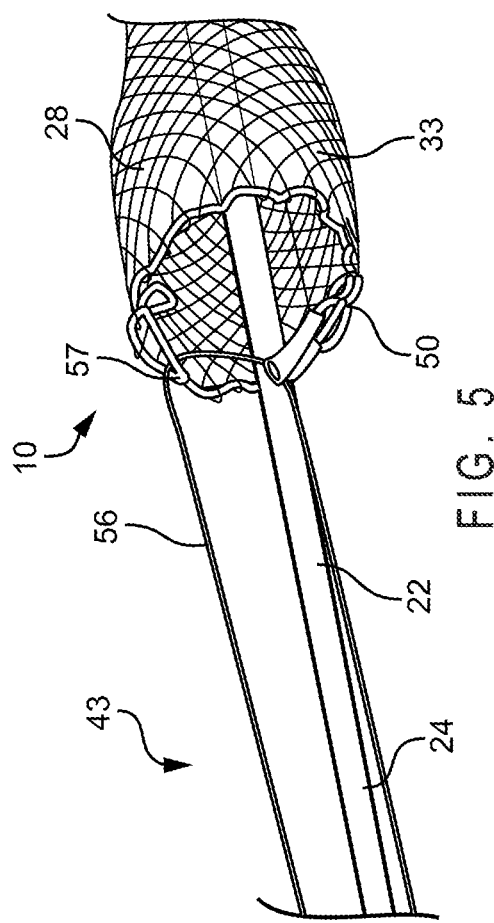
FIG. 5 illustrates the second section of the distal end of the stent delivery system shown in FIGS. 1A and 1B.

FIG. 5 illustrates the second section 43 of the distal end 24 of the system 10. As shown, the system 10 includes a distal tip 41, an inner shaft 22, a distal end portion 57 of the restraining member 56, and a distal end portion 60 of the release wire 59. The distal end 57 of restraining member 56, in this embodiment, is engaged with the grasping loops 48, 50 of the distal constraining member 46. As shown, the grasping loops 48, 50 of the distal constraining member are positioned on a distal end 33 of the stent 28. The stent 28 is still connected to the inner shaft 22 of the system 10 by the restraining member 59.

The materials used to manufacture the components of the stent delivery systems and mechanical dilator systems described herein may be any materials known to one skilled in the art that are suitable for use in patients. By way of non-limiting example, the shafts and sheaths may be formed from polytetrafluorothylene (PTFE) particularly when a low friction outer sheath is desirable. Nylon and HDPE may also be used for clarity. Additional possible materials include, but are not limited to the following, polyethylene ether ketone (PEEK), fluorinated ethylene propylene (FEP), perfluoro-alkoxy polymer resin (PFA), polyamide, polyurethane, high density or low density polyethylene, and nylon including multi-layer or single layer structures and the like and may also include reinforcement wires, braid wires, coils, coil springs and or filaments. The stent may be formed from but is not limited to the following materials: Nickel titanium alloys, for example, nitinol, stainless steel, cobalt alloys and titanium alloys. The loops of the constraining members may be made from common suture material as known in the art, for example polyester suture such as 4-0 Tevdek®, nylon, silk, polypropylene, ultra-high molecular weight polyethylene (UHMPE) and the like. The sutures may be monofilament, braided, twisted or multifilament. The loops and the retaining wires may also be made from a metallic alloy such as stainless steel or nickel titanium. In some embodiments, the stent, the loops and/or the retaining wires may be made from biodegradable materials. A number of bioabsorbable homopolymers, copolymers, or blends of bioabsorbable polymers are known in the medical arts. These include, but are not necessarily limited to, polyesters including poly-alpha hydroxy and poly-beta hydroxy polyesters, polycaprolactone, polyglycolic acid, polyether-esters, poly(p-dioxanone), polyoxaesters; polyphosphazenes; polyanhydrides; polycarbonates including polytrimethylene carbonate and poly(iminocarbonate); polyesteramides; polyurethanes;

polyisocyantes; polyphosphazines; polyethers including polyglycols polyorthoesters; expoxy polymers including polyethylene oxide; polysaccharides including cellulose, chitin, dextran, starch, hydroxyethyl starch, polygluconate, hyaluronic acid; polyamides including polyamino acids, polyester-amides, polyglutamic acid, poly-lysine, gelatin, fibrin, fibrinogen, casein, collagen.

Figure 6:
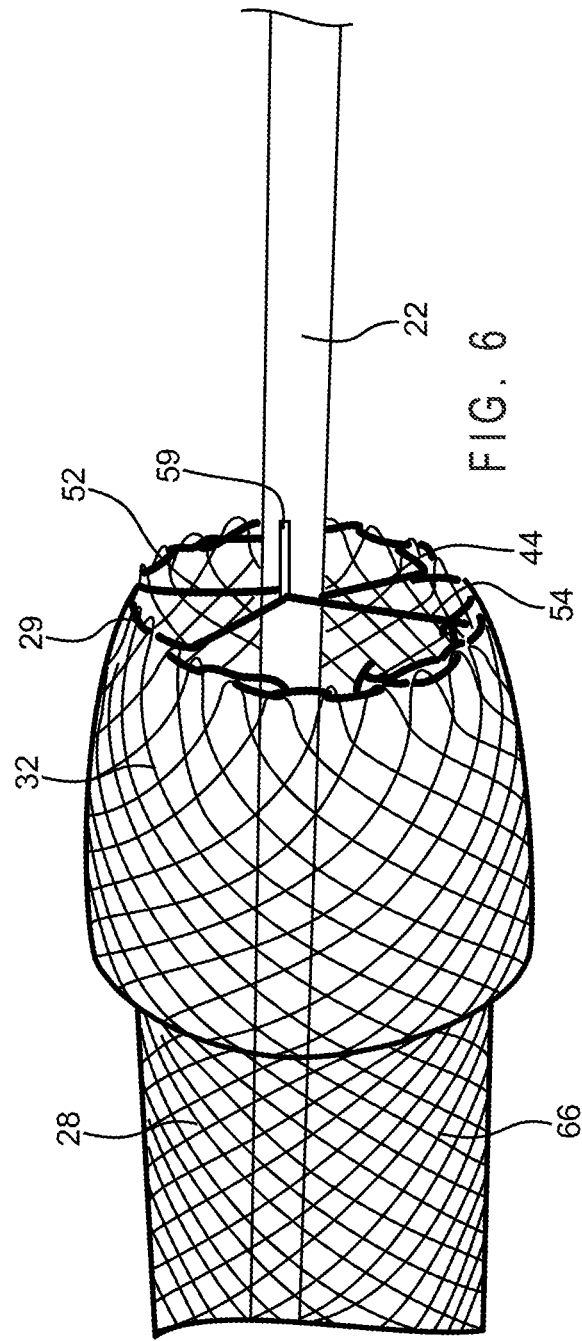
FIG. 6 illustrates an embodiment of a proximal end of the stent of the stent delivery system.

FIG. 6 illustrates an embodiment of a proximal end 32 of the stent 28 of the system 10. As shown, the stent 28 is shown in an expanded configuration 66. The proximal constraining member 44 may comprise one or more distal grasping loops 52, 54. In this embodiment, the proximal constraining member 44 comprises two loops 52, 54 that are interwoven through one or more peaks 29 of the stent 28 so that when pulled taut, the proximal constraining member 44 will collapse the peaks 29 of the stent 28 onto the inner shaft 22. The proximal grasping loops 52, 54 of the proximal constraining member 44 may be anchored at one or more points to better secure the stent 28 on the inner shaft 22. In the embodiment shown in FIG. 6, the proximal grasping loops 52, 54 are configured to remain attached to the stent 28 upon deployment within the lumen of a patient. In alternative embodiments, the proximal grasping loops 52, 54 may be configured to be released from the stent 28 upon deployment within the lumen of a patient. The proximal end 32 of the stent 28 remains connected to the inner shaft 22 even in the expanded configuration when the release wire 59 is engaged in the proximal grasping loops 52, 54 of the proximal constraining member 44. As shown, the release wire 59 extends within the inner shaft 22 and engages the two proximal grasping loops 52, 54 of the proximal constraining arrangement 44. In this embodiment, the proximal end 32 of the stent 28 is released from the constrained configuration 40 to the expanded configuration 66 by manipulation of a sheath.

In an alternative embodiment, the system 10 may include a second restraining member engaged with the proximal grasping loops of the proximal constraining member. In this alternative embodiment, the restraining member extends within a port disposed in the inner shaft and exits from the port at a proximal end of the inner shaft. The restraining member is configured to keep the distal end of the stent attached to the inner tube prior to deployment within the lumen of a patient while allowing the stent 28 to be released from the constrained configuration 40 to the expanded configuration 66. The proximal end stent 28 is released from the constrained configuration 40 to the expanded configuration 66 by manipulation in response to the proximal and distal manipulation of the second restraining member by the user of the system. In alternative embodiments, a second retaining member may be included in the system. The second restraining member may engage the proximal constraining member. In these embodiments, the second constraining member is configured to keep the proximal end of the stent attached to the inner tube prior to deployment within the lumen of a patient while allowing the stent 28 to be released from the constrained configuration 40 to the expanded configuration 66. The stent 28 is released from the constrained configuration 40 to the expanded configuration 66 by manipulation in response to the proximal and distal manipulation of the restraining member by the user of the system.

Figure 7:
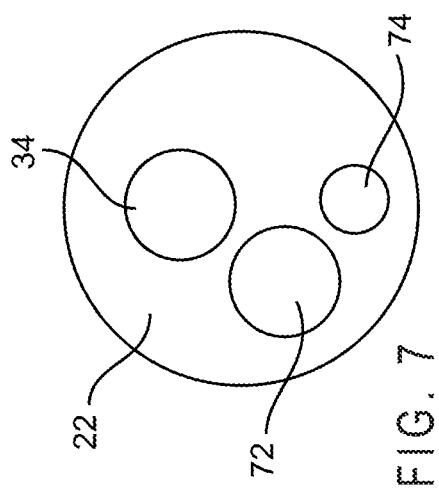
FIG. 7 illustrates a cross-section through an inner tube of the of the stent delivery system.

FIG. 7 illustrates a cross-section through an inner tube 22 of the of the stent delivery system 10. In this embodiment, the system 10 is provided in an over-the-wire configuration. In this over the wire configuration, the cross-section throughout the inner tube 22 is the same throughout its length. The inner tube 22 includes a suture lumen 34, a first lumen 72, and a second lumen 74. The suture lumen 34, the second lumen 72, and the third lumen 74 are disposed through the entire length of the inner tube 22. The suture lumen 34 may be used to facilitate the introduction of a medical device, such as a guidewire. The second lumen 72 is provided to receive at least a portion of the restraining member 56. The third lumen 74 is provided and is configured to receive a release wire 59 for use with the system 10. Each of the suture lumen 34, the second lumen 72, and the third lumen 74 are accessible from the proximal end 25 of the inner shaft 22. Exemplary materials for forming the shaft include, but are not limited to, metal alloys such as stainless steel, tantalum or its alloys, tungsten, platinum, gold, copper, palladium, rhodium, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon. In alternative embodiments, the inner tube 22 may further include additional lumens. In one embodiment, a fourth lumen may be included within the inner tube 22. In this embodiment, the fourth lumen may be used to provide a conduit for a second restraining member for the proximal constraining member 44 of the stent 28.

Figure 8:
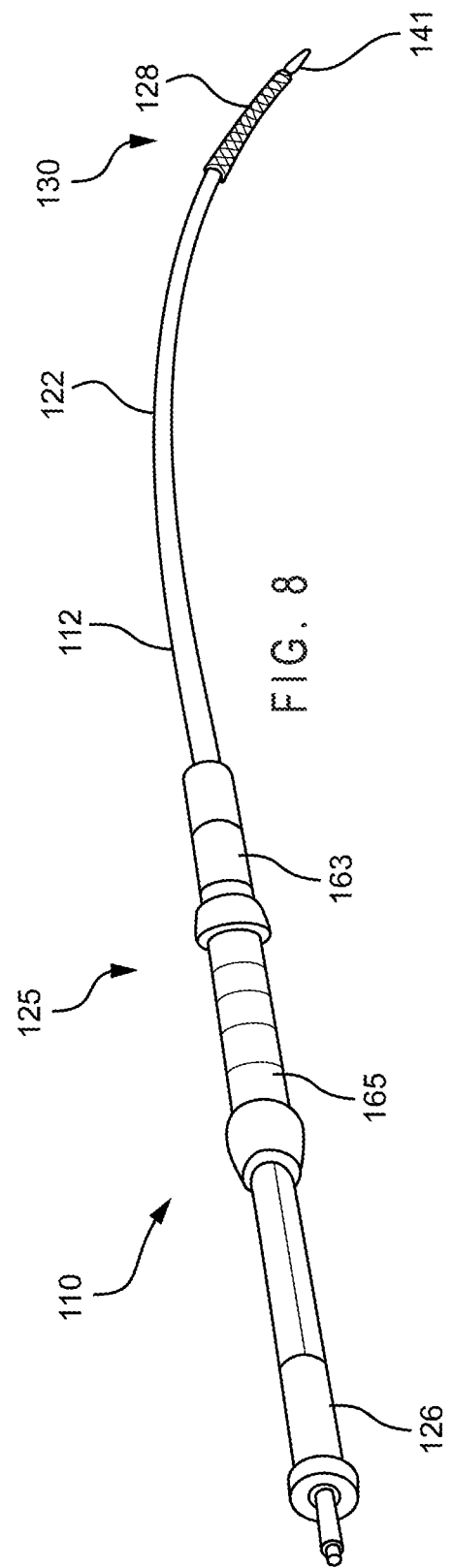
FIG. 8 illustrates an alternative embodiment a stent delivery system in accordance with embodiments of the present invention.

FIG. 8 illustrates an alternative embodiment of a stent delivery system 110 in accordance with embodiments of the present invention. The stent delivery system 110 includes an inner shaft 122 and a handle 126 at a proximal portion 125 of the system 110. A stent 128 (shown in FIG. 2) is positionable on a stent region 130 of the inner shaft 122 at a distal portion 131 of the delivery system 110. The stent delivery system 110 includes an outer sheath 112 slidably positionable over a portion the inner shaft 122 to cover the stent region 130 and the stent 128. The stent delivery system 110 may also include a guidewire extendable through a port of the inner shaft 122 through a distal tip 141 at the distal portion 131 of the delivery system 110. The handle 126 is comprised of at least two parts: a sheath shuttle 163 that is operatively connected to the outer sheath 112 and a constraining shuttle 165.

Figure 9A:
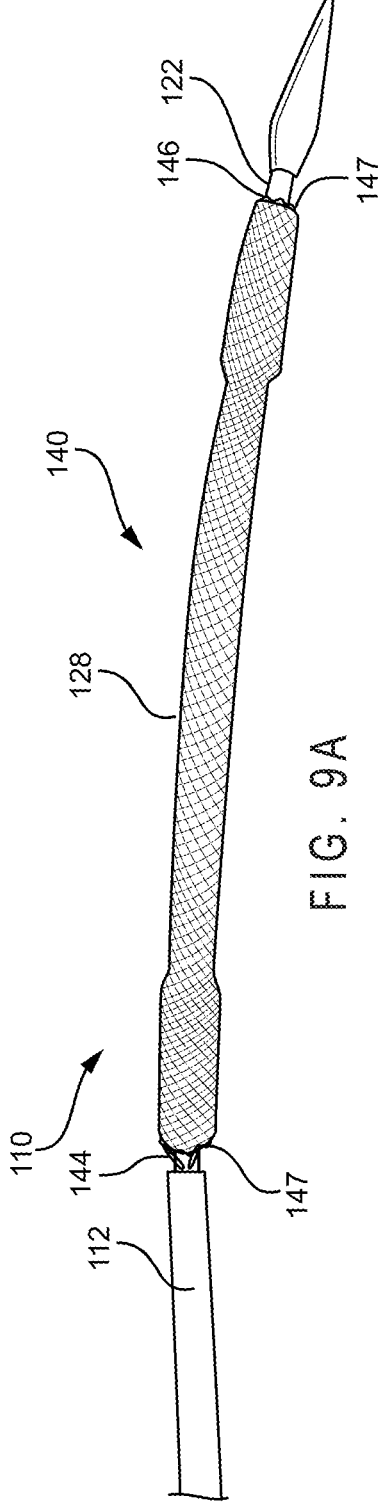
FIGS. 9A and 9B illustrate a side view of the stent delivery system shown in FIG. 8.

FIG. 9A illustrates a side view of the stent delivery system 110 shown in FIG. 8. As shown in FIG. 9A, the stent 128 is in a constrained configuration collapsed against the inner shaft 122. As shown, the sheath 112 is disposed over the stent 128 has been withdrawn proximally in order to provide a detailed look of the stent 128 in the constrained configuration 140. In some embodiments, the stent 128 may be a self-expanding stent. The stent 128 may be any kind of stent that has a tendency to radially collapse when a longitudinal force is applied to the ends of the stent. By way of non-limiting example, the stent 128 may be formed as a woven mesh formed from a metal or polymer or a laser cut pattern formed in a metal stent. The stent may also be formed from a bioabsorbable material. One example of a woven stent is the EVOLUTION® stent (Wilson-Cook Medical, Inc.). The stent 128 is held in the constrained configuration 140 by a mechanism that may be provided with or without an outer sheath 112. In one embodiment, that is described in detail below, that includes a proximal stent constraining arrangement 144 and a distal stent constraining arrangement 146 to longitudinally constrain the stent 128 and hold the stent 128 collapsed against the inner shaft 122. The proximal and distal stent constraining arrangements 144, 146 are operably connected to the constraining shuttle 165 of the handle 126. In particular, the proximal constraining arrangement 144 and the distal constraining arrangement 146 is connected to the handle through at least one port in the inner shaft 122, where a release wire (not shown) is disposed therethrough. As shown in FIG. 9A, the stent 128 is held compressed against the inner shaft 122 by the proximal and distal stent constraining members 144, 146 in a first position 147 applying longitudinal force to the stent 128 in opposite directions.

Figure 9B:
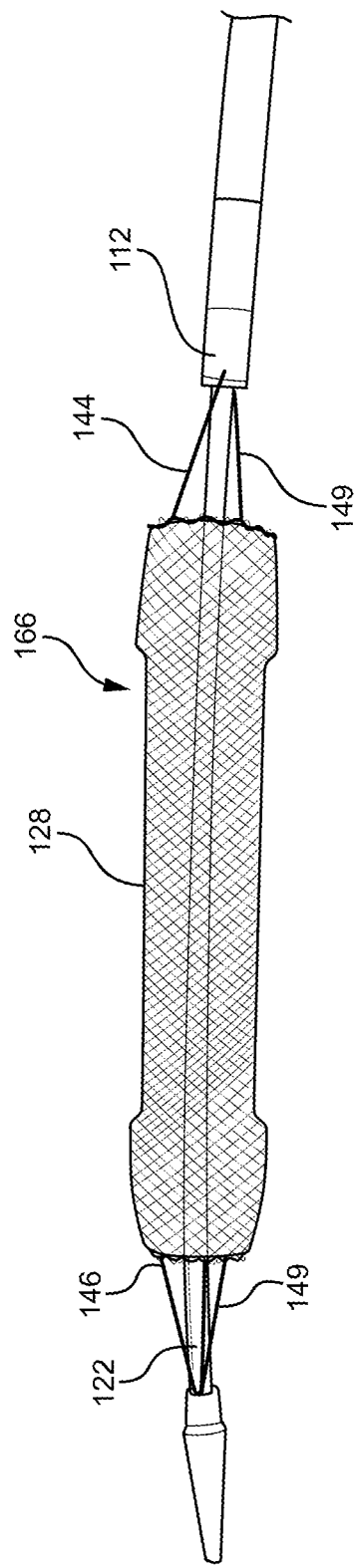

The stent 128 is shown in an expanded configuration 166 in FIG. 9B where the stent 128 is expanded away from the inner shaft 122. The proximal and distal constraining assemblies 144, 146 are in a second position 149 and remain connected to the stent 128 but the longitudinal force on the stent 128 has been removed to allow the stent 128 to expand. This second position 149 of the proximal constraining arrangement 144 and distal constraining arrangement 146 is achieved by manipulating a handle attached to the proximal constraining arrangement and the distal constraining arrangement 146 in a proximal direction.

Figure 10A:
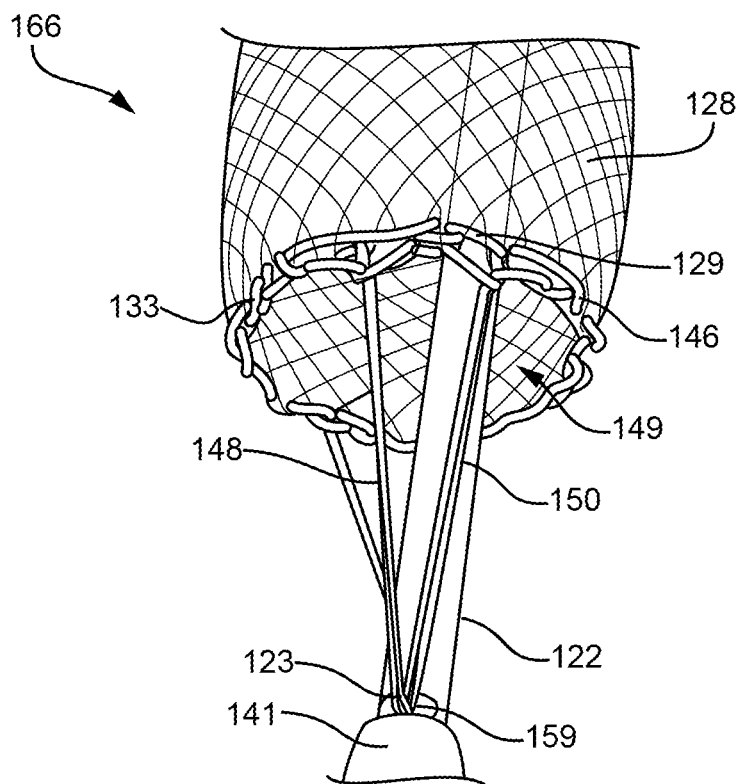
FIGS. 10A-10C illustrate a distal end of the stent delivery system of FIG. 8.

FIG. 10A shows a view of a first side of the distal end of the system 110. As shown, the stent 128 is shown in an expanded configuration 166 in FIG. 10 where the stent 128 is expanded away from the inner shaft 122. The distal constraining arrangement 146 is in a second position 149 and remain connected to the stent 128 but the longitudinal force on the stent 128 has been removed to allow the stent 128 to expand. As shown, the first and second distal restraining loops 148, 150 extend from a first opening 123 at the distal end 133 of the inner shaft 122. The first and second distal restraining loops 148, 150 are engaged are tethered to the inner tube 122 by a release wire 159. The proximal portion of the release wire (not shown) is engaged with the handle 126 of the system 110. In this embodiment, the first distal restraining loop 148 extends in a proximal direction and is interwoven with the peaks of the distal end 133 of the stent 128. After traversing the peaks of the stent 128, the first distal restraining loop 148 exits the distal end 133 of the stent and extends in a distal direction toward the distal tip 141 of the system 110. Similarly, the second distal restraining loop 150 extends in a proximal direction and is interwoven with the peaks of the distal end 133 of the stent 128. After traversing the peaks of the stent 128, the second distal restraining loop 150 exits the distal end 133 of the stent 128 and extends in a distal direction toward the distal tip 141 of the system 110. In this embodiment, the distal constraining arrangement 146, in this embodiment, includes a first distal loop 148, and a second distal loop 150. The distal loops 148, 150 may be interwoven through one or more peaks of the stent so that the distal loops 148, 150 when pulled taut will collapse the peaks of the stent onto the inner shaft. The distal grasping loops may be positioned on opposing sides of the stent, as provided in this embodiment. In particular, the first distal loop 148 is interwoven through six peaks of one side of the distal end 133 of the stent 128 halfway around the stent circumference. The second distal loop 150 is interwoven through six peaks 129 of the distal end 133 of the stent 128 on the side opposite of the first distal loop 148 halfway around the circumference.

Upon release of the release wire 159 by the user of the system 110, the first distal restraining loop 148 and the second distal restraining loop 150 is also released, allowing the distal end 133 of the stent 128 to be deployed within the lumen of the patient. The release wire 159 may be frictionally engaged with a portion of the inner shaft 122 of the system 110 to hold the release wire 159 in position until the stent 128 is in the proper position for release. The first distal restraining loop 148 and the second distal restraining loop 150 moves the distal end 133 of the stent 128 so that the longitudinal tension exerted on the stent 128 is relaxed when the first distal restraining loop 148 and the second distal restraining loop 150 of the distal constraining arrangement 146 are farther apart and the stent 128 expands uniformly due to the uniform release of the tension on the stent 128 by the distal constraining arrangement 144.

Figure 10B:
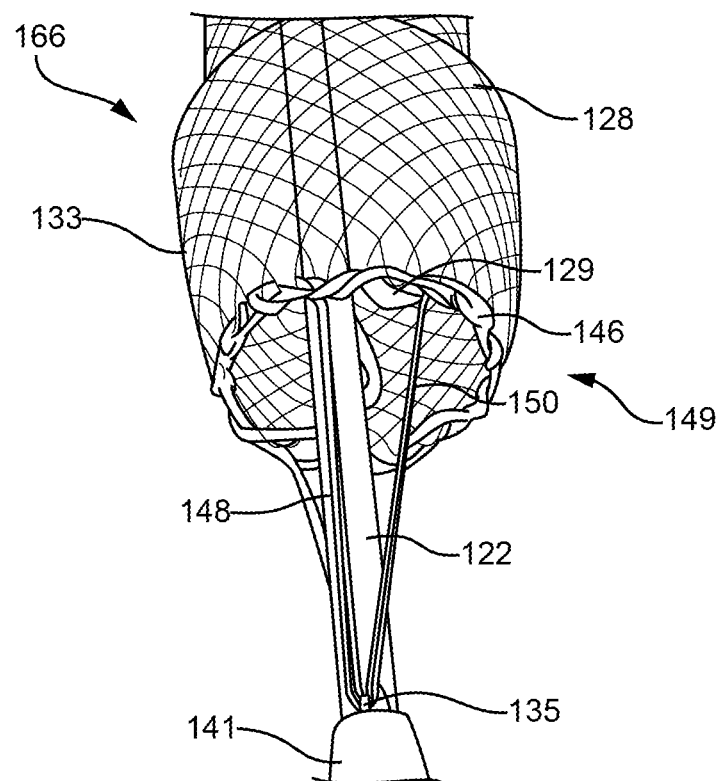

FIG. 10B shows a view second side of the distal end of the system 110. As shown in this embodiment, a second opening 135 proximal to the distal tip 141 is in communication with a suture lumen 134 of the inner shaft 122. The second opening 135 is positioned on an opposite side of the inner shaft 122 than the first opening 123. The first distal restraining loop 148 enters into a suture lumen 134 of inner tube 122 of the system 110 through the second opening 135 of the inner shaft. Upon entering the lumen 134 of the inner tube 122 of the system 110, the first distal restraining loop 148 extends through the length of the inner tube 122 and engages with a handle 126. The constraining shuttle 165 of the handle 126 allows for control of the distal constraining assembly member in order to move the stent 28 from the constrained configuration 140 to the expanded configuration 166 so that the release of the tension on the stent 128 is uniform within the patient's lumen. Similarly, the second distal restraining loop 150 enters into the suture lumen 134 of inner tube 122 of the system 110 through the second opening 135 of the inner shaft 122. Upon entering the suture lumen 134 of the inner tube 122 of the system 110, the second distal restraining loop 150 extends through the length of the inner tube and engages with a handle 126.

Figure 10C:
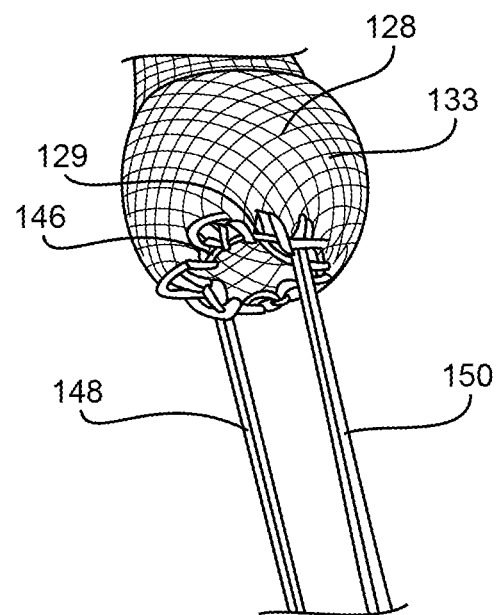

FIG. 10C shows an alternative arrangement for the distal constraining arrangement 146. In this embodiment, the distal constraining arrangement 146, in this embodiment, includes a first distal loop 148, and a second distal loop 150. The distal loops 148, 150 may be interwoven through one or more peaks of the stent so that the distal loops 148, 150 when pulled taut will collapse the peaks of the stent onto the inner shaft. The distal grasping loops may be positioned on opposing sides of the stent, as provided in this embodiment. In particular, the first distal loop 148 is interwoven through eight peaks of one side of the distal end 133 of the stent 128 halfway around the stent circumference. The second distal loop 150 is interwoven through six peaks of the distal end 133 of the stent 128 on the side opposite of the first distal loop 148 halfway around the circumference.

Figure 11:
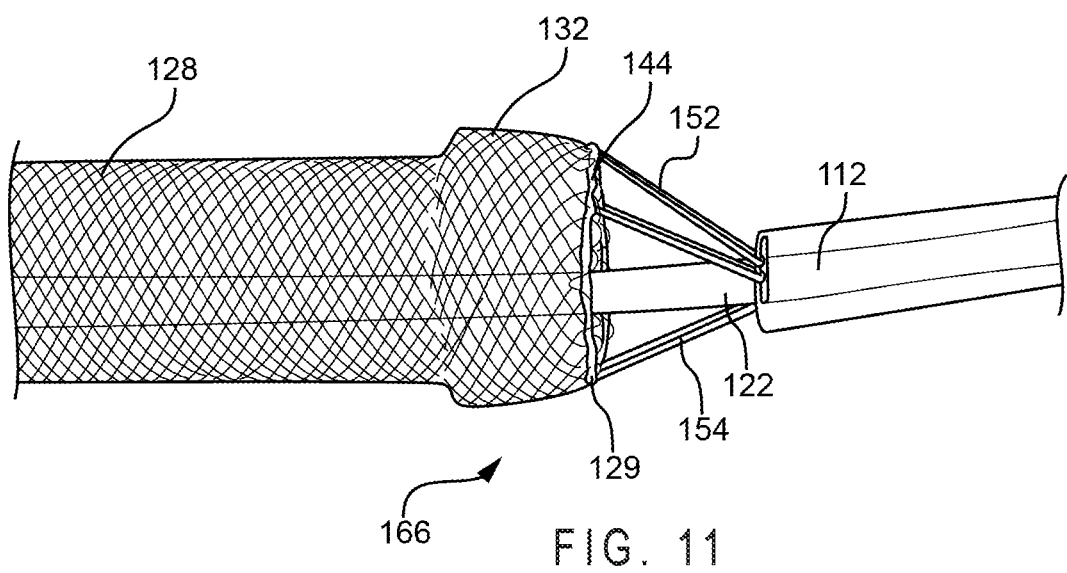
FIG. 11 illustrates a proximal end of the stent delivery system of FIG. 8.

FIG. 11 shows a view of the proximal end of the system 10. As shown, the stent 128 is shown in an expanded configuration 166 in FIG. 11 where the stent 128 is expanded away from the inner shaft 122. The proximal constraining arrangement 144 is in a second position and remains connected to the stent 128 but the longitudinal force on the stent 128 has been removed to allow the stent 128 to expand. The proximal constraining arrangement 144, in this embodiment, includes a first proximal loop 152, and a second distal loop 154. The proximal loops 152, 154 may be interwoven through one or more peaks of the stent so that the proximal loops 152, 154 when pulled taut will collapse the peaks of the stent 128 onto the inner shaft 122. The proximal restraining loops 152, 154 may be positioned on opposing sides of the stent 128, as provided in this embodiment. In particular, the first proximal loop 152 is interwoven through six peaks of one side of the proximal end 132 of the stent 128 halfway around the circumference. The second proximal loop 154 is interwoven through six peaks of the proximal end 132 of the stent 128 on the side opposite of the first proximal loop 152 halfway around the circumference. In alternative embodiments, the first proximal loop 152 and the second proximal loop 154 may be interwoven through more peaks of the stent 128 or fewer peaks of the stent 128.

As shown, the first proximal loop 152 and the second proximal loop 154 are tethered to the inner shaft 122 by a release wire 159. The proximal portion of the release wire (not shown) is engaged with a handle 126 of the system 110. The release wire 159 may be proximally withdrawn to release the first proximal loop 152 and the second proximal loop 154. In this embodiment, the first proximal restraining loop 152 extends in a proximal direction and is interwoven with the peaks of the proximal end 132 of the stent 128. After traversing the peaks of the stent 128, the first proximal restraining loop 152 exits the proximal end 132 of the stent 128 and extends in a proximal direction toward the handle 126 of the system. The first proximal restraining loop 152 enters into a suture lumen 134 of inner tube 122 of the system 110. Upon entering the lumen 134 through an opening 136 of the inner shaft 122 of the system 110, the first proximal restraining loop 152 extends through the inner tube 122 and engages with the constraining shuttle 165 of the handle 126. The handle 126 allows for control of the proximal constraining arrangement 144 in order to move the stent 128 from the constrained configuration 140 to the expanded configuration 166 so that the release of the tension on the stent 128 is uniform within the patient's lumen.

Similarly, the second proximal constraining loop 154 extends in a distal direction and is interwoven with the peaks of the proximal end 132 of the stent 128. After traversing the peaks of the stent 128, the second proximal restraining loop 154 exits the proximal end 132 of the stent 128 and extends in a proximal direction toward the handle 126 of the system 110. The second proximal constraining loop 154 enters into a suture lumen 134 of inner tube of the system through an opening of the inner shaft 122. Upon entering the lumen 134 of the inner tube 122 of the system 110, the second proximal constraining loop 154 extends through the inner tube 122 and engages with the constraining shuttle 165 of the handle 126. Upon release of the release wire 159 by the user of the system 110, the proximal end of the restraining member is also released, allowing the proximal end 132 of the stent 126 to be deployed within the lumen of the patient. The release wire 159 may be frictionally engaged with a portion of the inner shaft 122 of the system 110 to hold the release wire 159 in position until the stent 128 is in the proper position for release. The first proximal loop 152 and the second proximal loop 154 moves the proximal end 132 of the stent 128 so that the longitudinal tension exerted on the stent 128 is relaxed when first proximal loop 152 and the second proximal loop 154 of the proximal constraining member 144 are farther apart and the stent 128 expands uniformly due to the uniform release of the tension on the stent 28 by the distal constraining member 44.

Figure 12:
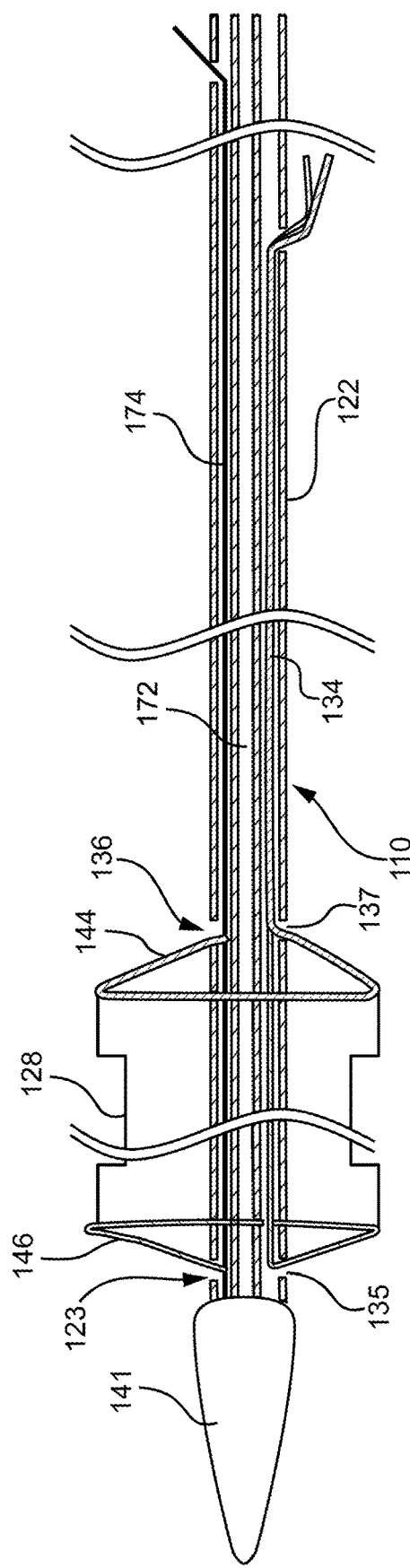
FIG. 12 illustrates a sectional view of the stent delivery system of FIG. 8.

FIG. 12 is a schematic view of an embodiment of the present invention. The stent delivery system 110 includes an inner shaft 122 and a handle (not shown) at a proximal portion 127 of the system 110. A stent 128 is positionable on a stent region 130 of the inner shaft 122 at a distal portion 131 of the delivery system 110. The stent 128 is shown in an expanded position. As shown, the proximal and distal stent constraining arrangements 144, 146 are operably connected to the handle 126 and are disposed through the suture lumen 134. The stent delivery system 110 may also include a guidewire extendable through a second lumen 172 of the inner shaft 122 through a distal tip 141 at the distal portion 131 of the delivery system 110. A release wire is disposed in through the third lumen 174 and is engaged with a portion of the proximal and distal constraining arrangements 144, 146 to anchor the proximal and distal constraining arrangements 144, 146 to the inner shaft 122.

Figure 13A:
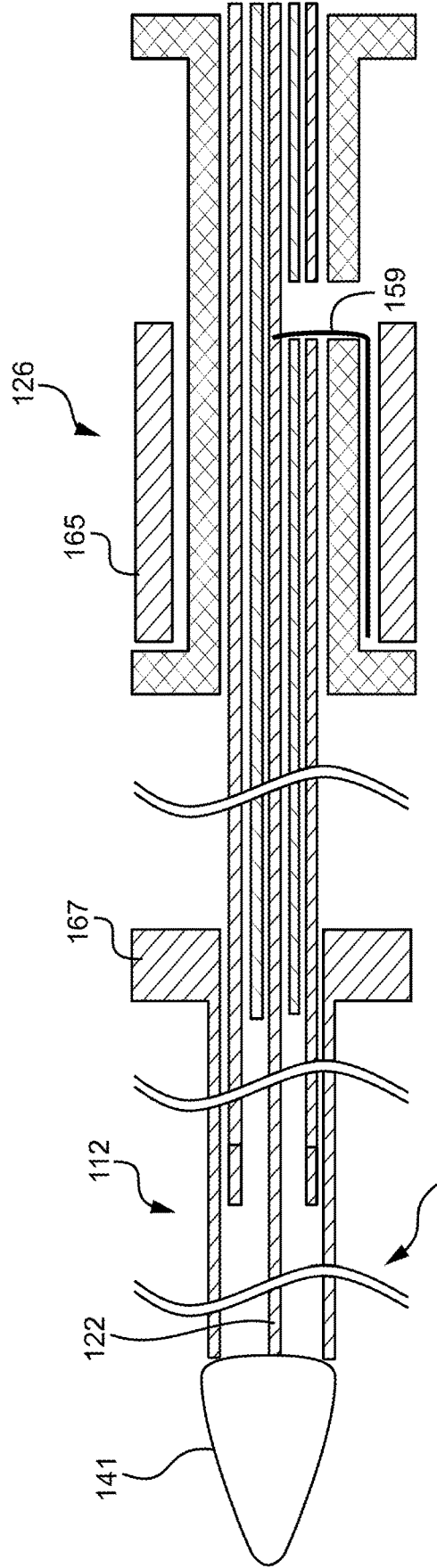

Operation of an embodiment of the system is illustrated in FIG. 13A and FIG. 13B. For ease of depiction, the stent 128 is not shown. In FIG. 13A, the system includes an inner shaft 122 and a handle 126 at a proximal portion 127 of the system 110. The handle 126 includes a constraining shuttle 165 and a sheath shuttle 167. A sheath 112 is operably connected to the sheath shuttle 167 of the handle 126. As shown, the proximal and distal stent constraining arrangements 144, 146 are operably connected to the constraining handle 165 and are disposed through the suture lumen 134. The sheath 112 and sheath shuttle 167 is distally positioned upon the system 110 in the stent attachment portion 130 of the system 110. The constraining shuttle 165 of the handle 126 are also positioned distally in a locked position and maintaining the stent 128 in a constrained position 140. As shown in FIG. 13B, in order to deploy the stent 128, the user proximally moves the sheath shuttle 167, which uncovers the stent 128. The user then unlocks the constraining shuttle 165 of the handle 126 and moves the constraining shuttle 165 in a proximal direction. The proximal movement of the constraining shuttle 165 moves the stent from the constrained position to the expanded position. Once the stent 128 is placed in the correct position, the user may release the release wire 159 and deploy the stent 128 within the vessel of the patient.

FIG. 14 illustrates a sectional view of an alternate embodiment of a stent delivery system 210. The stent delivery system 210 includes an inner shaft 222 and an outer shaft 221. A stent 228 is positionable on a stent region 230 of the inner shaft 222 at a distal portion 231 of the delivery system 210. The stent 228 is shown in an expanded configuration 266 in FIG. 14 where the stent 228 is expanded away from the inner shaft 222. The distal constraining assembly 246 is in a second position and remain connected to the stent 228 but the longitudinal force on the stent 228 has been removed to allow the stent 228 to expand. This second position of the proximal and distal constraining member 244, 246 is manipulated in a proximal direction through the use of a handle 226 attached to the system 210. The inner shaft 222 includes a first, suture lumen 234, a second lumen 272, a third lumen 274. As shown, the distal stent constraining arrangement 246 is disposed through the suture lumen 234. A release wire 259 is disposed through the third lumen 274 and is engaged with a portion of the proximal and distal constraining arrangements 244, 246 to anchor the proximal and distal constraining arrangements 244, 246 to the inner tube 222. The stent delivery system 210 may also include a guidewire extendable through the second lumen 272 of the inner shaft 222 through a distal tip 241 at the distal portion 231 of the delivery system 210. The outer shaft 221 includes a first lumen 280 and a second lumen 282. The inner shaft 222 is concentrically positioned within the first lumen 280 of the outer shaft 221. The proximal stent constraining arrangement 244 is disposed through the second lumen 282 of the outer shaft 221. In this embodiment, the proximal constraining arrangement 244 and the distal constraining arrangement 246 are positioned within different lumens and do not interfere with one another. Thus, the proximal constraining arrangement 244 and the distal constraining arrangement 246 can operate independently from each other. With this embodiment, the proximal constraining arrangement 244 and the distal constraining arrangement 246 allow for the distal end 231 of the stent 228 and the proximal end 232 of the stent 228 can be moved from the constrained position 240 to the expanded position 266 at different times and by different amounts.

FIG. 15 illustrates a cross-section through an outer shaft 221 of an embodiment of the present invention. In this embodiment, the system 210 is provided in an over-the-wire configuration. In this over the wire configuration, the cross-section throughout the outer tube 221 is the same throughout its length. The outer tube 221 includes a first lumen 280 and a second lumen 282. The first lumen 280 and the second lumen 282 are disposed through the entire length of the outer tube 221. The second lumen 282 is provided to receive at least a portion of the distal restraining arrangement 244. The first lumen 280 may be used to facilitate reception of the inner shaft 222. Each of the first lumen 280 and the second lumen 282 are accessible from the proximal end of the outer shaft 221. Exemplary materials for forming the outer shaft 221 include, but are not limited to, metal alloys such as stainless steel, tantalum or its alloys, tungsten, platinum, gold, copper, palladium, rhodium, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon. In alternative embodiments, the outer tube 221 may further include additional lumens.

FIG. 16 is a sectional view of an embodiment of the present invention. The stent delivery system 310 includes an inner shaft 322 and a handle 326 at a proximal portion 327 of the system 310. A stent retaining region 330 is present at the proximal end 327 of the system in order to provide an area for placement of a stent for use with the system 310. The inner shaft 322 includes a first, suture lumen, a second lumen, and a third lumen. The outer shaft 321 includes a first lumen and a second lumen 382. The inner shaft 322 is disposed within the second lumen 382 of the outer shaft 321 such that the inner shaft 322 is concentric with the outer shaft 321. The distal loops 348, 350 of the distal constraining arrangement 346 are disposed within the suture lumen of the inner shaft 322. The proximal loops of the proximal constraining arrangement 344 are disposed within the first lumen of the outer shaft. The handle 326 is disposed about the outer surface of the outer shaft 321 and includes a hub 363, a sheath shuttle 367, and a constraining shuttle 365. A sheath 312 is operably connected to the sheath shuttle 367 of the handle 326. As shown, the proximal loops of the proximal constraining arrangement 344 exit the suture lumen of the inner shaft 322 and engage with at least a portion of the constraining shuttle 365. Similarly, the distal loops of the distal constraining arrangement 344 exit the first lumen 380 of the outer shaft 321 and are operably connected with at least a portion of the constraining shuttle 365. In this embodiment, the proximal loops of the proximal constraining arrangement 344 and the distal loops of the distal constraining arrangement 346 are operably connected to a brake assembly 390 disposed within the housing of the constraining shuttle 365. The brake assembly 390, in this embodiment, comprises a washer 392 and a break spring 394 disposed about the surface of the outer shaft 321 of the system 310. The spring 394 of the brake assembly 390 keeps the washer 392 at an angle with respect to the outer shaft 321 and keeps the brake washer 392 ready to engage with the shaft upon activation of the brake assembly 390. This arrangement prevents the brake 390 from failing to engage and this arrangement decreases the time taken for the break to engage upon activation.

In one embodiment, the distal loops of the distal constraining arrangement 346 are positioned underneath the brake assembly 390 and are attached to the constraining shuttle 365 at the proximal end 327 of the system 310. The proximal loops of the proximal constraining arrangement 344 maybe looped around the brake assembly 390 in order to accommodate the additional length required in order to make the proximal constraining arrangement 344 operable with this embodiment of the brake assembly 390. In this embodiment, the distal loops 3118, 350 of the distal constraining arrangement 346 may be pulled proximally up to three times further then the proximal loops of the proximal constraining arrangement 344 upon operation of the constraining shuttle 365 of the handle 326 in the proximal direction. One of ordinary skill in the art will understand that alternative arrangements may be utilized with this aspect of the present invention. As will be as will be discussed, the brake assembly 390 allows for staged deployment of the proximal end of a stent and the distal end of a stent. A release wire is disposed through the second lumen and is engaged with a portion of the proximal and distal constraining arrangements 344, 346 to anchor the proximal and distal constraining arrangements 344, 346 to the inner tube 322.

Figure 17C:
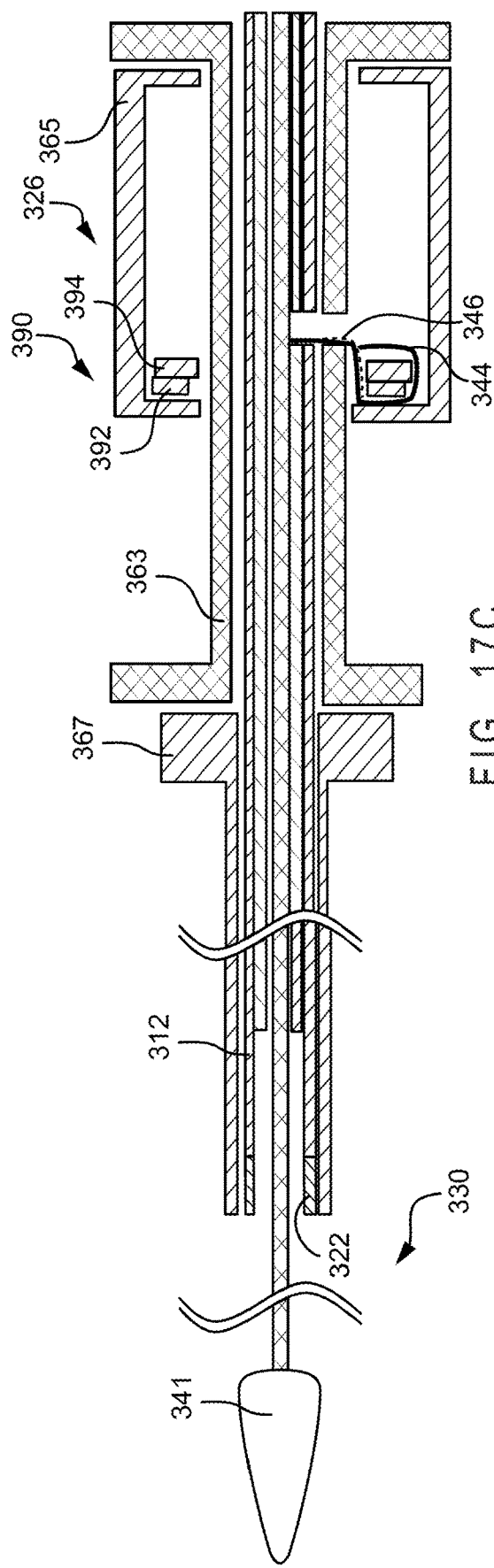

FIGS. 17A-17C illustrate operation of this embodiment of the system 310 of the present invention. Referring to FIG. 17A, the sheath shuttle 367 has been moved in a proximal direction and in abutting relation with the hub 363 of the handle 326. Upon moving the sheath shuttle 367 in the proximal direction, the sheath attached to the sheath shuttle 367 is retracted in the proximal direction and uncovers the stent. In this position, the stent is still in the constrained configuration 340. The constraining shuttle 365 of the handle 326 is in a distal position with respect to the hub 363 of the handle 326. In this distal position, the proximal constraining arrangement 344 and the distal constraining arrangement 346 remain in the taut configuration which maintains the stent in the collapsed configuration 340. In some embodiments, the system 310 may include a locking apparatus to maintain the constraining shuttle 365 in this distal position. In these embodiments, the lock assembly may prevent premature deployment of the stent prior to proper positioning of the stent within the target lumen of the patient. As shown by FIG. 17A, the brake washer 392 and the brake spring 394 are engaged. When the brake assembly 390 is engaged, the proximal constraining arrangement 344 and the distal constraining arrangement 346 are maintained in the taut configuration. This brake assembly 390 also prevents premature deployment expansion of the stent prior to proper positioning of the stent within the lumen of the patient.

Referring now to FIG. 17B, the constraining shuttle 365 has been moved in a proximal direction with respect to the hub 363 of the handle 326. The proximal movement of the constraining shuttle 365 disengages the brake assembly 390. In this embodiment, the washer 392 of the brake assembly 390 is pulled into a vertical configuration. In addition, the brake spring 394 of the brake assembly 390 is compressed, which allows for the washer to be positioned vertically within the body of the constraining shuttle 365. Upon disengagement, the entire brake assembly 390 is able to move in conjunction with the movement of the constraining shuttle 365 of the handle 326. This movement of the brake assembly 390, allows for the proximal constraining arrangement 344 and the distal constraining arrangement 346 to move in the proximal direction.

Referring now to FIG. 17C, the constraining shuttle 365 has been fully moved in the proximal direction with respect to the hub 363 of the handle 326. As shown the brake assembly 390 has also been moved in the proximal direction. In this position, the stent 328 is now moved from the constrained configuration 340 to the expanded configuration 366. In this embodiment, this proximal movement of the proximal constraining arrangement 344 and the distal constraining arrangement 346 release the stent 328 from the constrained configuration 340 to the expanded configuration 366. In alternative embodiments, the system 310 may allow for staged a release of the distal end and the proximal end of the stent. The stent, while in the expanded configuration, is still connected to the system 310 by the proximal constraining arrangement 344 and the distal constraining arrangement 346. The stent 328 may be repeatedly moved between the constrained configuration and the expanded configuration by manipulating the proximal constraining arrangement 344 and the distal constraining arrangement 346 either in a proximal direction or a distal direction until the stent 328 is properly positioned through the use of the constraining shuttle 365. Upon moving the constraining shuttle 365 in the distal direction the distal loops of the distal constraining configuration 346 are pulled first, which constrains the distal end of the stent prior to the proximal end of the stent which allows for any additional material of the loops of the proximal constraining arrangement 344 to also be pulled by the constraining handle 365. Upon removal of any slack material of the proximal constraining arrangement 344, the distal end and the proximal end of the stent are constrained simultaneously.

Figure 18:
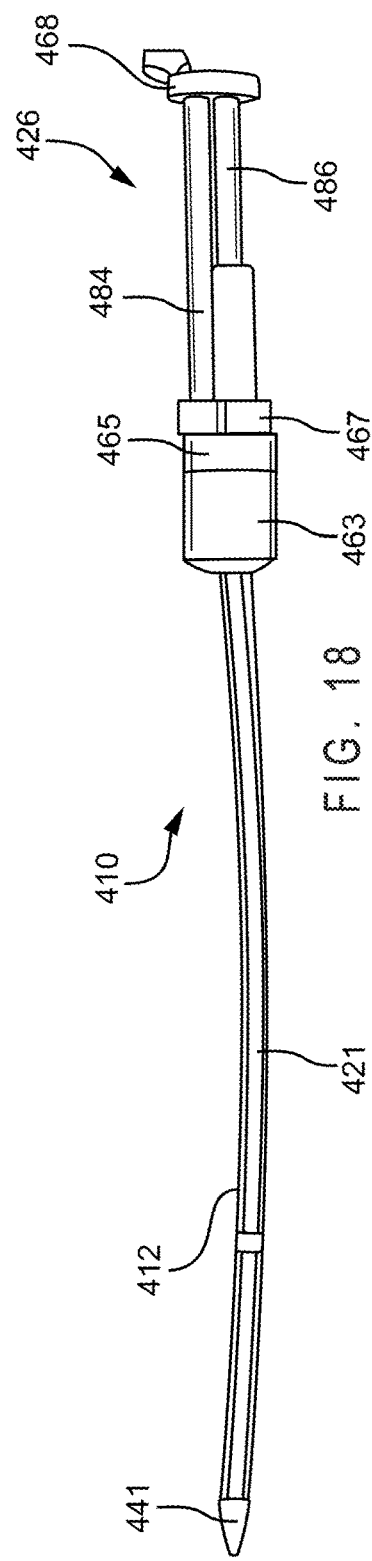
FIG. 18 illustrates of an alternative embodiment of a handle assembly of a stent delivery system.

FIG. 18 illustrates of an alternative embodiment of a handle assembly 426 of a stent delivery system 410. The handle assembly 426 includes a hub 463, a sheath shuttle 467, a constraining shuttle 465, and a handle back stop 468 positioned on a proximal end of the handle assembly 426. A first conduit 484 and a second conduit 486 of the hub 463 are engaged with the handle back stop 468. In a particular embodiment, as shown in FIG. 18, the first conduit 484 and the second conduit 486 are cylindrical tubules. An outer shaft 421 is disposed through a lumen of the first conduit 484. As shown, the sheath shuttle 467 is engaged with an outer surface of the first conduit 484 and is configured to travel longitudinally with respect to the first conduit 484. The sheath 412 is operably connected to the sheath shuttle 467 of the handle 426. In some embodiments, the sheath 412 may include additional features, including, but not limited to, the ability to be torn away from the device or the ability to crumple. The constraining shuttle 465 is engaged with an outer surface of the second conduit 484 and is configured to travel longitudinally with respect to the second conduit is disposed on the second conduit 484. As shown in the embodiment of FIG. 18, the constraining shuttle 465 is positioned distal to the sheath shuttle 467. In this particular embodiment, the constraining shuttle 465 is configured to move proximally following movement of the sheath shuttle 467 in the proximal direction. In alternative embodiments, the constraining shuttle 465 and the sheath shuttle 467 may be configured such that the constraining shuttle 465 may be moved independent of the movement of the sheath shuttle 467.

Figure 19:
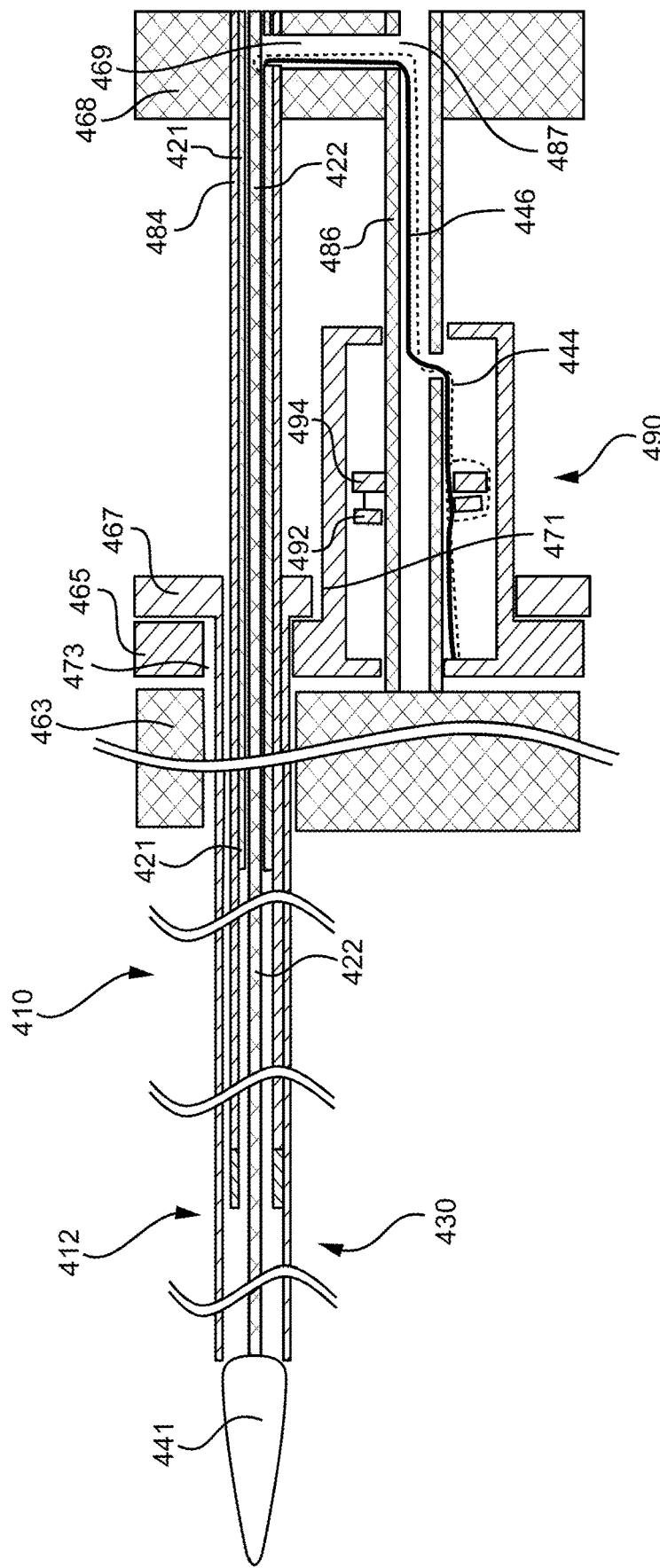
FIG. 19 is a schematic view of the handle assembly of FIG. 18.

FIG. 19 is a schematic view of an embodiment of the system 410 and the handle assembly 426. The handle assembly 426 includes a hub 463, a sheath shuttle 467, a constraining shuttle 465, and a handle back stop 468 positioned on a proximal end of the handle assembly 326. A first conduit 484 and a second conduit 486 of the hub 463 are engaged with the handle back stop 468. The first conduit 484 and the second conduit 486 each have a lumen disposed therethrough. An outer shaft 421 and an inner shaft 422 are disposed through a lumen of the first conduit 484. As shown, proximal loops of a proximal constraining arrangement 444 exit a lumen of the inner shaft 422 and engage with at least a portion of the constraining shuttle 465. Similarly, distal loops of the distal constraining arrangement 446 exit a lumen of the outer shaft 421 and are operably connected with at least a portion of the constraining shuttle 465. In this embodiment, the proximal loops of the proximal constraining arrangement 444 and the distal loops of the distal constraining arrangement 446 are operably connected to a brake assembly 490 disposed within the housing of the constraining shuttle 465. A pathway 469 connecting the first conduit 484 and the second conduit 486 is provided within the handle back stop 468 to allow the proximal loops of the proximal constraining arrangement 444 and the distal loops of the distal constraining arrangement 446 to pass from the outer shaft 421, inner shaft 422, and the first conduit 484 into a lumen of the second conduit 486. The proximal loops of the proximal constraining arrangement 444 and the distal loops of the distal constraining arrangement 446 enter into the lumen of the second conduit 486 through a port 487. The brake assembly 490, in this embodiment, comprises a washer 492 and a break spring 494 disposed about the surface of the outer shaft 421 of the system 410. The break spring 494 of the brake assembly 490 keeps the washer 492 at an angle with respect to the outer shaft 421 and keeps the brake washer 492 ready to engage with the shaft upon activation of the break. This arrangement prevents the brake from failing to engage and decreases the time taken for the break to engage upon activation.

In one embodiment, the distal loops of the distal constraining arrangement 446 are positioned underneath the brake assembly 490 and are attached to the constraining shuttle 465 at the proximal end. The proximal loops of the proximal constraining arrangement 444 maybe looped around the brake assembly 490 in order to accommodate the additional length required in order to make the proximal constraining arrangement 444 operable with this embodiment of the handle brake assembly 490. In this embodiment, the distal loops of the distal constraining arrangement 446 may be pulled proximally up to three times further then the proximal loops of the proximal constraining arrangement 444 upon operation of the constraining shuttle 465 of the handle 426 in the proximal direction. One of ordinary skill in the art will understand that alternative arrangements may be utilized with this aspect of the present invention. As will be as will be discussed, the brake arrangement 490 allows for staged deployment of the proximal end of a stent and the distal end of a stent. A release wire may be disposed in through the second lumen 472 and is engaged with a portion of the proximal and distal constraining arrangements 444, 446 to anchor the proximal and distal constraining arrangements 444, 446 within the system 410.

As shown, the sheath shuttle 467 is engaged with an outer surface of the first conduit 484 and the sheath 412 is operably connected to the sheath shuttle 467 of the handle 426. The constraining shuttle 465 is engaged with an outer surface of the second conduit 484 and is configured to travel longitudinally with respect to the second conduit 484. The sheath shuttle 467 includes an opening 471. The opening 471 allows the sheath shuttle 467 to move along the first conduit 484 while not interfering with the constraining shuttle 465 and the second conduit. Likewise, the constraining shuttle 465 also includes an opening 473. The opening 473 allows the constraining shuttle 465 to move along the second conduit 486 while not interfering with the sheath shuttle 467 and the first conduit 484.

FIGS. 20A and 20B illustrate operation of this embodiment of the system 410 of the present invention. Referring to FIG. 20 A, the sheath shuttle 465 has been moved in a proximal direction and in abutting relation with the handle back stop 468 of the handle 426. Upon moving the sheath shuttle 467 in the proximal direction, the sheath 412 attached to the sheath shuttle 467 is retracted in the proximal direction and uncovers the stent 428. In this position, the stent 428 is still in the constrained configuration 440. The constraining shuttle 465 of the handle 426 is in a distal position with respect to the hub 463 of the handle 426. In this distal position, the proximal constraining arrangement 444 and the distal constraining arrangement 446 remain in the taut configuration which maintains the student in the collapsed configuration. In some embodiments, the system 410 may include a locking apparatus to maintain the constraining shuttle in this distal position. In these embodiments the lock may prevent premature deployment of the stent prior to proper positioning of the stent within the target lumen of the patient. As shown by FIG. 20A, the washer 492 and the brake spring 494 are engaged. When the brake assembly 490 is engaged, the proximal constraining arrangement 444 and the distal constraining arrangement 446 are maintained in the taut configuration. This brake assembly 490 also prevents premature deployment expansion of the stent 428 prior to proper positioning of the stent 428 within the lumen of the patient.

Referring now to FIG. 20B, the constraining shuttle 465 has been fully moved in the proximal direction with respect to the hub 463 of the handle 426. The proximal movement of the constraining shuttle 465 this engages the brake assembly 490. In this embodiment, the washer 494 of the brake assembly 490 is pulled into a vertical configuration. In this position, the stent is now moved from the constrained configuration 440 to the expanded configuration 464. In this embodiment, this proximal movement of the proximal constraining arrangement 444 and the distal constraining arrangement 446 release the stent from the constrained configuration 440 to the expanded configuration 466. In alternative embodiments, the system 410 may allow for staged a release of the distal end and the proximal end of the stent. The stent, while in the expanded configuration, is still connected to the system 410 by the proximal constraining configuration 444 and the distal constraining configuration 446. The stent may be repeatedly moved between the constrained configuration 440 and the expanded configuration 466 by moving the constraining shuttle 465 distally with respect to the hub 463 of the handle 426. Upon moving the constraining shuttle 465 in the distal direction the distal loops 448, 450 of the distal constraining configuration 446 are pulled first, which constrains the distal end of the stent prior to the proximal end of the stent which allows for any additional material of the proximal loops of the proximal constraining arrangement 444 to also be pulled by the constraining handle 465. Upon removal of any slack material of the proximal constraining arrangement 444, the distal end 433 and the proximal end 432 are constrained simultaneously.

FIG. 21 illustrates of schematic view of an alternative embodiment of a handle assembly 526 of a stent delivery system 510. The stent delivery system 510 includes an inner shaft 522, outer shaft 521, and a handle 526 at a proximal portion of the system 510 having a handle back stop 568. A stent retaining region 530 is present at the distal end 527 of the system 510 in order to provide an area for placement of a stent for use with the system 510. The inner shaft 522 includes a suture lumen, a second lumen, and a third lumen. The outer shaft 521 includes a first lumen, and a second lumen. The inner shaft 522 may be disposed within the first lumen of the outer shaft 521 such that the inner shaft 521 is concentric with the outer shaft 521. The distal loops of the distal constraining arrangement 546 are disposed within the suture lumen of the inner shaft 522. The proximal loops of the proximal constraining arrangement 544 are disposed within the first lumen of the outer shaft 521. The handle assembly 526 is disposed about the outer surface of the outer shaft 521 and includes a hub 563, a sheath shuttle 567, and a constraining shuttle 565. A sheath 512 is operably connected to the sheath shuttle 567 of the handle 526. The constraining shuttle 565 comprises an outer shuttle 576 and an inner shuttle 578. As shown, the proximal loops of the proximal constraining arrangement 544 exit the first lumen of the outer shaft 521 and engage with at least a portion of the constraining shuttle 565. Similarly, the distal loops of the distal constraining arrangement 546 exit the inner shaft 522 and are operably connected with at least a portion of the constraining shuttle 565. In this embodiment, the proximal loops of the proximal constraining arrangement 544 are operably connected to a brake assembly 590 disposed within the housing of the constraining shuttle 565. The brake assembly 590, in this embodiment, comprises a washer 592 and a break spring 594 disposed about the surface of the outer shaft 521 of the system 510. The spring 594 of the brake assembly 590 keeps the washer 592 at an angle with respect to the outer shaft 521 and keeps the brake washer 592 ready to engage with the shaft 521 upon activation of the brake assembly 590. This arrangement prevents the brake from failing to engage and this arrangement decreases the time taken for the brake to engage upon activation. The distal loops of the distal constraining arrangement 546 are connected to the inner shuttle 578. A compressed spring 579 is engaged with the inner shuttle 578 and maintains the distal end of the stent in the compressed position.

FIGS. 22A and 22B illustrate operation of this embodiment of the system 510 of the present invention. Referring to FIG. 22 A, the sheath shuttle 567 has been moved in a proximal direction and in abutting relation with the handle back stop 568 of the handle 526. Upon moving the sheath shuttle 567 in the proximal direction, the sheath 512 attached to the sheath shuttle 565 is retracted in the proximal direction and uncovers the stent. In this position, the stent is still in the constrained configuration. The constraining shuttle 565 of the handle 526 is in a proximal position with respect to the hub 563 of the handle 526. In this proximal position, the proximal constraining arrangement 544 and the distal constraining arrangement 546 remain in the taut configuration which maintains the stent in the collapsed configuration. In some embodiments, the system 510 may include a locking apparatus to maintain the constraining shuttle 565 in this distal position. In these embodiments, the lock may prevent premature deployment of the stent prior to proper positioning of the stent within the target lumen of the patient.

Referring now to FIG. 22 B, the constraining shuttle 565 has been fully moved in the distal direction with respect to the hub of the handle. The distal movement of the constraining shuttle 565 this engages the brake assembly 590. In this embodiment, the washer 594 of the brake assembly 590 is pulled into a vertical configuration. In this position, the stent is now moved from the constrained configuration to the expanded configuration. In this embodiment, this distal movement of the proximal constraining arrangement 544 and the distal constraining arrangement 546 release the stent from the constrained configuration 540 to the expanded configuration 566. In alternative embodiments, the system 510 may allow for staged a release of the distal end and the proximal end of the stent. The stent, while in the expanded configuration 566, is still connected to the system 510 by the proximal constraining configuration 544 and the distal constraining configuration 546. The stent may be moved from the expanded configuration to the constrained configuration by moving the constraining shuttle 565 in the proximal direction with respect to the hub 563 of the handle assembly 526. Upon moving the constraining shuttle 565 in the proximal direction the distal loops of the distal constraining configuration 546 are pulled first, which constrains the distal end of the stent prior to the proximal end of the stent which allows for any additional material of the proximal loops of the proximal constraining arrangement 544 to also be pulled by the constraining handle 565. Upon removal of any slack material of the proximal constraining arrangement 544, the distal end and the proximal end of the stent are constrained. In this embodiment, the distal end of the stent is constrained prior to the proximal end of the stent. Due to the distal constraining arrangement 546 traveling a different path than the proximal constraining arrangement 544 and the sequence of constraining the distal end of the stent prior to the proximal end of the stent, the amount of force needed to constrain the stent may be reduced.

FIG. 23 illustrates of schematic view of an alternative embodiment of a handle assembly 626 of a stent delivery system 610. The stent delivery system 610 includes an inner shaft 622 and a handle 626 at a proximal portion 627 of the system 610, and a handle back stop 668. A stent retaining region 630 is present at the proximal end 627 of the system 610 in order to provide an area for placement of a stent for use with the system 610. The inner shaft 622 includes a suture lumen, a second lumen, and a third lumen. The outer shaft 621 includes a first lumen, and a second lumen. The inner shaft 622 is disposed within the second lumen of the outer shaft 621 such that the inner shaft 622 is concentric with the outer shaft 621. The distal loops of the distal constraining arrangement 646 are disposed within the suture lumen of the inner shaft 622. The proximal loops of the proximal constraining arrangement 644 are disposed within the outer shaft 621. The handle assembly 626 is disposed about the outer surface of the outer shaft 621 and includes a hub 663, a sheath shuttle 667, and a constraining shuttle 665. A sheath 612 is operably connected to the sheath shuttle 667 of the handle 626. As shown, the proximal loops of the proximal constraining arrangement 644 exit the lumen of the inner shaft 621 and engage with at least a portion of the constraining shuttle 665. Similarly, the distal loops of the distal constraining arrangement 646 exit the lumen of the outer shaft 621 and operably connected with at least a portion of the constraining shuttle 665. In this embodiment, the proximal loops of the proximal constraining arrangement 644 are operably connected to a first brake assembly 690 disposed within the housing of the constraining shuttle 665. Likewise, the distal loops of the distal constraining arrangement 646 are operably connected to a second brake assembly 691 disposed within the housing of the constraining shuttle 665. The second brake assembly 691 is positioned proximal to the first brake assembly 690. The first brake assembly 690, in this embodiment, comprises a washer 692 and a break spring 694 disposed about the surface of the outer shaft 621 of the system 610. The break spring 694 of the first brake assembly 690 keeps the washer 692 at an angle with respect to the outer shaft 621 and keeps the brake washer 692 ready to engage with the outer shaft 621 upon activation of the first brake assembly 690. This arrangement prevents the first brake assembly 690 from failing to engage and this arrangement decreases the time taken for the first brake assembly 690 to engage upon activation. The second brake assembly 691 also comprises a washer 693 and a break spring 695 disposed about the surface of the outer shaft 621 of the system 610. The second break assembly 691 further includes a projection 696 extending from the washer 693. A leaf spring 697 and collar 698 are positioned within the interior surface of the handle assembly 626. The projection 696 of the second brake assembly 691 is configured to allow the leaf spring 697 to slide over second brake assembly 691 when the constraining shuttle 665 is moved distally and configured to engage the leaf spring 697 when the constraining shuttle 665 is moved proximally.

Figure 24C:
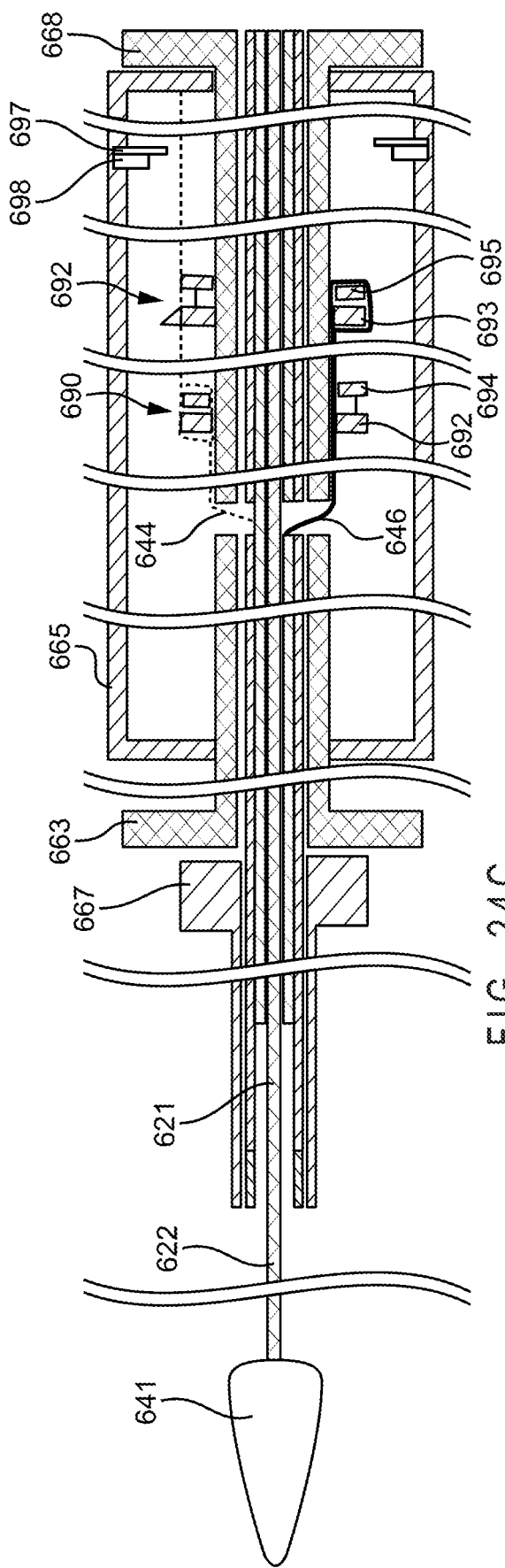

FIGS. 24A-24C illustrate operation of this embodiment of the system 610 of the present invention. Referring to FIG. 24 A, the sheath shuttle 667 has been moved in a proximal direction and in abutting relation with the handle back stop 668 of the handle assembly 626. Upon moving the sheath shuttle 667 in the proximal direction, the sheath 612 attached to the sheath shuttle 667 is retracted in the proximal direction and uncovers the stent 628. In this position, the stent is still in the constrained configuration 640. The constraining shuttle 665 of the handle assembly 626 is in a proximal position with respect to the hub 663 of the handle 665. In this proximal position, the proximal constraining arrangement 644 and the distal constraining arrangement 646 remain in the taut configuration which maintains the stent in the collapsed configuration 640. In some embodiments, the system 610 may include a locking apparatus to maintain the constraining shuttle 665 in this distal position. In these embodiments the lock may prevent premature deployment of the stent prior to proper positioning of the stent within the target lumen of the patient. As shown by FIG. 24A, the first brake assembly 690 and the brake spring 692 are engaged. When the first brake assembly 690 is engaged, the proximal constraining arrangement is maintained in the taut configuration. Likewise, the second brake assembly 691 and the brake spring 693 are engaged. When the second brake assembly 691 is engaged, the distal constraining arrangement is maintained in the taut configuration. This first brake assembly 690 and the second brake assembly 691 also prevent premature deployment expansion of the stent 628 prior to proper positioning of the stent 628 within the lumen of the patient.

Referring now to FIG. 24 B, the constraining shuttle 665 has been fully moved in the distal direction with respect to the hub 663 of the handle. The distal movement of the constraining shuttle 665 disengages the second brake assembly 691. The proximal end of the constraining shuttle 665 disengages the second brake assembly 691 and unlocks it, which causes the second brake assembly 691 to move in the distal direction. This distal movement of the second brake assembly 691 releases the tension on the distal constraining arrangement 646 and the distal end of the stent is expanded. As the constraining shuttle 665 continues to move in the distal direction, the second brake assembly 691 moves along with it and comes into contact with the first brake assembly 690 and disengages it. The disengaged first brake assembly 690 moves in the distal direction and the tension on the proximal constraining arrangement 644 and the proximal end of the stent is expanded. In this embodiment, this distal movement of the proximal constraining arrangement 644 and the distal constraining arrangement 646 release the stent from the constrained configuration to the expanded configuration. In alternative embodiments, the system 610 may allow for staged a release of the distal end and the proximal end of the stent. The stent, while in the expanded configuration 646, is still connected to the system 610 by the proximal constraining configuration 644 and the distal constraining configuration 646. The stent may be moved from the expanded configuration to the constrained configuration by moving the constraining shuttle 665 in the proximal direction with respect to the hub 663 of the handle.

FIG. 24C illustrates how the stent may be moved from the expanded configuration 666 to the constrained configuration 640. Upon moving the constraining shuttle 665 in the proximal direction, the leaf spring 697 engages the projection 696 of the second brake assembly 691 and moves it in the proximal direction. The leaf spring and the collar apply sufficient force to move the second brake assembly 691 in the proximal direction. This proximal movement of the second brake assembly 691 causes the distal loops of the distal constraining configuration 646 to be pulled taut, which constrains the distal end 633 of the stent prior to the proximal end of the stent. The second brake assembly 691 is also engaged, which prevents the distal end 633 of the stent from being released from the constrained position 640. As the constraining shuttle 665 is moved further in the proximal direction, the first brake assembly 691 is also pulled proximally. Upon removal of any slack material of the proximal constraining arrangement 644, the distal end and the proximal end are constrained. When both the distal end and the proximal end of the stent are constrained, the leaf spring 697 is released from the second brake assembly 691, as the amount of force of constraining sheath 665 exceeds the force of the leaf spring 697. In this embodiment, the distal end of the stent is constrained prior to the proximal end of the stent.

Figure 25:
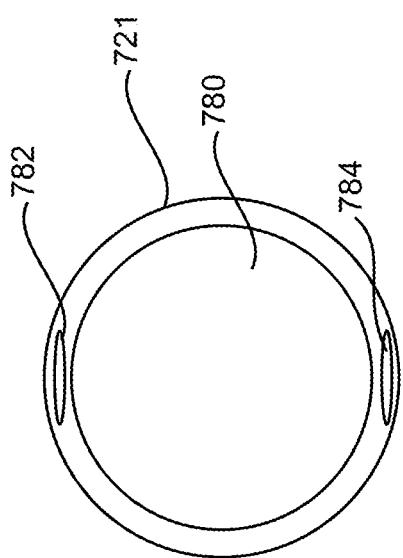
FIG. 25 illustrates a cross-section through an alternative outer shaft of the present invention.

FIG. 25 illustrates a cross-section through an alternative outer shaft 721 of an embodiment of the present invention. In this embodiment, the system 710 is provided in an over-the-wire configuration. In this over the wire configuration, the cross-section throughout the outer tube 721 is the same throughout its length. The outer tube 721 includes a first lumen 780, a second lumen 782, and a third lumen 784. The first lumen 780, a second lumen 782, and a third lumen 784 are disposed through the entire length of the outer tube 721. The first lumen 780 may be used to facilitate the introduction of a medical device, such as a guidewire. The second lumen 782 and third lumen 784 is provided to receive one proximal loop, respectively, of the proximal constraining member 744. Each of first lumen 780, a second lumen 782, and a third lumen 784, are accessible from the proximal end of the outer shaft 721. Exemplary materials for forming the shaft include, but are not limited to, metal alloys such as stainless steel, tantalum or its alloys, tungsten, platinum, gold, copper, palladium, rhodium, or a superelastic alloys, such as nitinol or polymers that can be provided with sufficient shore hardness, such as Pebax, Peek, polyimide, liquid crystal polymers (LCP) such as Vectran, polyethylene, polyethylene terephthalate and Nylon. In alternative embodiments, the inner tube may further include additional lumens. In one embodiment, a fourth lumen may be included within the inner tube. In this embodiment, the fourth lumen may be used to provide a conduit for a second restraining member for the proximal constraining member of the stent.

FIG. 26 illustrates a perspective view of an alternative embodiment of a handle assembly 826 of a stent delivery system 810. The stent delivery system 810 includes an inner shaft 822 and a handle 826 at a proximal portion of the system 810. The inner shaft 822 includes a suture lumen, a second lumen, and a third lumen. The outer shaft 821 includes a first lumen and a second lumen. The inner shaft 822 is disposed within the outer shaft 821 such that the inner shaft 822 is concentric with the outer shaft 821. The distal loops of the distal constraining arrangement 846 are disposed within the suture lumen 834 of the inner shaft 822. The proximal loops of the proximal constraining arrangement 844 are disposed within the first lumen 880 of the outer shaft 821. The handle assembly 826 is disposed about the outer surface of the outer shaft 821 and includes a hub 863, a sheath shuttle 867, and a constraining shuttle 865. A sheath 812 is operably connected to the sheath shuttle 867 of the handle 826. As shown, the proximal loops of the proximal constraining arrangement 844 exit the first lumen 880 of the outer shaft 821 and engage with at least a portion of the constraining shuttle 865. Similarly, the distal loops of the distal constraining arrangement 846 exit the suture lumen 834 of the inner shaft 822 and operably connected with at least a portion of the constraining shuttle 865. In this embodiment, the proximal loops of the proximal constraining arrangement 844 are operably connected to proximal shuttle 878 disposed within the housing of the constraining shuttle 865. Likewise, the distal loops of the distal constraining arrangement 846 are operably connected to a distal shuttle 876 disposed within the housing of the constraining shuttle 865. The proximal shuttle 876 and the distal shuttle 876 are configured to engage with the constraining shuttle 865 and each have dedicated tracks to allow for longitudinal movement with respect to the constraining shuttle 865. As shown, the constraining shuttle 865 has been moved in the distal direction with respect to the hub 863 of the handle 826. The distal movement of the constraining shuttle 865 first engages distal shuttle 876 and moves it in the distal direction. In this position, the stent 828 is now moved from the constrained configuration 840 to the expanded configuration 866. In this embodiment, this distal movement of the distal shuttle 876 releases the distal end 833 of the stent 828 from the constrained configuration 840 to the expanded configuration 866. Once the distal end 833 of the stent 828 is deployed, the constraining shuttle 865 is continually moved in the distal direction and disengages from the proximal shuttle 878. Subsequently, the constraining shuttle 865 engages the proximal shuttle 878 and moves it in the distal direction. The distal movement of the proximal shuttle 878 releases proximal end of the stent from the constrained configuration 840 to the expanded configuration 866. The stent, while in the expanded configuration, is still connected to the system 810 by the proximal constraining arrangement 844 and the distal constraining arrangement 846.

FIG. 27 illustrates operation of this embodiment of the handle 826 of the present invention. The constraining shuttle 865 of the handle 826 is in a distal position with respect to the hub 863 of the handle 826. In this distal position, the proximal constraining arrangement 844 and the distal constraining arrangement 846 remain in the taut configuration which maintains the stent in the collapsed configuration 840. In some embodiments, the system 810 may include a locking apparatus to maintain the constraining shuttle 865 in this distal position. In these embodiments the lock may prevent premature deployment of the stent prior to proper positioning of the stent within the target lumen of the patient. As shown by FIG. 27, the proximal shuttle 878 and distal shuttle 876 are also positioned proximally and in locked position. A ratchet mechanism may be added to prevent the user from changing the direction of movement of the shuttle during operation.

The stent may be moved from the expanded configuration 866 to the constrained configuration 868 by moving the constraining shuttle 865 in the proximal direction with respect to the hub 863 of the handle 826. Upon moving the constraining shuttle 865 in the proximal direction the distal shuttle 868 is engaged and the distal loops of the distal constraining configuration 846 are pulled first, which constrains the distal end of the stent prior to the proximal end of the stent. Further movement of the constraining shuttle 865 in the proximal direction also engages the proximal shuttle 878 and begins to pull the proximal end of the stent taut. Upon removal of any slack material of the proximal constraining arrangement 844, the distal end and the proximal end of the stent are constrained. In this embodiment, the distal end of the stent is constrained prior to the proximal end of the stent. Due to the distal constraining arrangement 846 traveling a different path than the proximal constraining arrangement 844 and the sequence of constraining the distal end of the stent prior to the proximal end of the stent, the amount of force needed to constrain the stent may be reduced.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. A stent delivery system, comprising,
   an elongate shaft including a proximal portion, a distal portion, at least one lumen extending at least partially therethrough, and a stent receiving portion on the distal portion of the elongate shaft;
   a stent positioned on the stent receiving portion of the elongate shaft, the stent having a first configuration and a second configuration;
   a proximal constraining arrangement engaged with a proximal end of the stent, the proximal constraining arrangement comprising a first proximal constraining member having a proximal portion, a second proximal portion, and a distal portion and a second proximal constraining member having a first proximal portion and a distal portion, the distal portion of the first proximal constraining member engaged with a first proximal portion of the stent and the distal portion of the second proximal constraining member engaged with a second proximal portion of the stent;
   a distal constraining arrangement engaged with a distal end of the stent, the distal constraining arrangement comprising a first distal constraining member having a proximal portion, a second proximal portion and a distal portion, and a second distal constraining member having a proximal portion and a distal portion, the distal portion of the first distal constraining member engaged with a first distal portion of the stent and the distal portion of the second proximal constraining member engaged with a second distal portion of the stent;
   a handle assembly comprising a first shuttle operably connected to the proximal constraining arrangement and a second shuttle operably connected to the distal constraining arrangement; and,
   a brake assembly positioned within the handle assembly, the proximal constraining arrangement being coupled to the brake assembly;
   wherein the proximal constraining arrangement and the distal constraining arrangement applies an axial mechanical force to at least a portion of the stent in the first configuration.

2. The stent delivery system of claim 1, wherein the first proximal constraining member and the second proximal constraining member are interwoven into the proximal end of the stent.

3. The stent delivery system of claim 1, wherein a proximal suture arrangement is disposed at the proximal end of the stent and the first proximal constraining member and the second proximal constraining member are interwoven into the proximal suture arrangement.

4. The stent delivery system of claim 1, wherein the first distal constraining member and the second distal constraining member are interwoven into the distal end of the stent.

5. The stent delivery system of claim 1, wherein a distal suture arrangement is disposed at the distal end of the stent and the first distal constraining member and the second distal constraining member are interwoven into the distal suture arrangement.

6. The stent delivery system of claim 1, wherein the first shuttle and the second shuttle are axially moveable relative to the handle assembly.

7. The stent delivery system of claim 1, wherein the second shuttle is positioned within the first shuttle.

8. The stent delivery system of claim 1, wherein the handle assembly further includes a spring engaged with the second shuttle.

9. The stent delivery system of claim 1, wherein the elongate shaft further comprises a first lumen and a second lumen.

10. The stent delivery system of claim 9, wherein the distal constraining assembly is at least partially disposed in the first lumen.

11. The stent delivery system of claim 1, wherein a release wire is disposed through the elongate shaft and releasably engaged with the proximal constraining arrangement and the distal constraining arrangement.

12. The stent delivery system of claim 11, wherein the stent is in the first configuration upon proximal movement of the first shuttle and the second shuttle from a first position to a second position.

13. The stent delivery system of claim 1, wherein the first shuttle and the second shuttle are axially moveable from a first position and a second position.

14. A stent delivery system, comprising,
   an inner elongate shaft including a proximal portion, a distal portion, at least one lumen extending at least partially therethrough, and a stent receiving portion on the distal portion of the inner elongate shaft;
   an outer elongate shaft including a proximal portion, a distal portion, at least one lumen extending at least partially therethrough, the inner elongate shaft extending coaxially at least partially within the lumen of the outer elongate shaft, the outer elongate shaft moveably positionable relative to the inner elongate shaft;
   a stent positioned on the stent receiving portion of the inner elongate shaft, the stent having a first configuration and a second configuration;
   a proximal constraining arrangement engaged with a proximal end of the stent, the proximal constraining arrangement comprising a first proximal constraining member having a proximal portion, a second proximal portion, and a distal portion, and a second proximal constraining member having a proximal portion and a distal portion, the distal portion of the first proximal constraining member engaged with a first proximal portion of the stent and the distal portion of the second proximal constraining member engaged with a second proximal portion of the stent;
   a distal constraining arrangement engaged with a distal end of the stent, the distal constraining arrangement comprising a first distal constraining member having a proximal portion, a second proximal portion, and a distal portion, and a second distal constraining member having a proximal portion and a distal portion, the distal portion of the first distal constraining member engaged with a first distal portion of the stent and the distal portion of the second proximal constraining member engaged with a second distal portion of the stent;

a release wire disposed through the inner elongate shaft and releasably engaged with portion of the proximal constraining arrangement and the distal constraining arrangement member;

a handle assembly comprising a first shuttle operably connected to the proximal constraining arrangement and a second shuttle operably connected to the distal constraining arrangement; and, a brake assembly positioned within the handle assembly, the proximal constraining arrangement being coupled to a portion of the brake assembly;

wherein the proximal constraining arrangement and the distal constraining arrangement applies an axial mechanical force to at least a portion of the stent in the first configuration.

* * * * *